(12) United States Patent
Bhakdi

(10) Patent No.: US 12,326,386 B2
(45) Date of Patent: Jun. 10, 2025

(54) SYSTEMS AND METHODS FOR IDENTIFYING RARE CELLS

(71) Applicant: X-Zell, Inc., Wilmington, DE (US)

(72) Inventor: Sebastian Chakrit Punyaratabandhu Bhakdi, Bangkok (TH)

(73) Assignee: X-Zell, Inc., Wilmington, DE (US)

( * ) Notice: Subject to any disclaimer, the term of this patent is extended or adjusted under 35 U.S.C. 154(b) by 483 days.

(21) Appl. No.: 17/556,434

(22) Filed: Dec. 20, 2021

(65) Prior Publication Data

US 2022/0113231 A1 Apr. 14, 2022

Related U.S. Application Data

(63) Continuation of application No. 16/083,194, filed as application No. PCT/US2017/020905 on Mar. 6, 2017, now Pat. No. 11,226,271.

(60) Provisional application No. 62/430,542, filed on Dec. 6, 2016, provisional application No. 62/313,250, filed on Mar. 25, 2016, provisional application No. 62/313,366, filed on Mar. 25, 2016, provisional application No. 62/304,452, filed on Mar. 7, 2016.

(51) Int. Cl.

| | |
|---|---|
| G01N 1/30 | (2006.01) |
| C11D 1/66 | (2006.01) |
| C11D 3/04 | (2006.01) |
| C11D 3/20 | (2006.01) |
| C11D 3/37 | (2006.01) |
| C11D 3/43 | (2006.01) |
| C12N 11/08 | (2020.01) |
| C12N 11/089 | (2020.01) |
| G01N 1/36 | (2006.01) |
| G01N 33/574 | (2006.01) |
| G06T 7/00 | (2017.01) |

(52) U.S. Cl.
CPC .............. *G01N 1/30* (2013.01); *C11D 1/667* (2013.01); *C11D 3/046* (2013.01); *C11D 3/2003* (2013.01); *C11D 3/2065* (2013.01); *C11D 3/3776* (2013.01); *C11D 3/43* (2013.01); *C12N 11/08* (2013.01); *C12N 11/089* (2020.01); *G01N 1/36* (2013.01); *G06T 7/0012* (2013.01); *G06T 7/0014* (2013.01); *C11D 2111/12* (2024.01); *C11D 2111/44* (2024.01); *G01N 2001/302* (2013.01); *G01N 2001/305* (2013.01); *G01N 33/574* (2013.01)

(58) Field of Classification Search
None
See application file for complete search history.

(56) References Cited

U.S. PATENT DOCUMENTS

| | | |
|---|---|---|
| 3,826,365 A | 7/1974 | Mercade |
| 3,983,033 A | 9/1976 | De Latour |
| 4,664,796 A | 5/1987 | Graham et al. |
| 4,927,749 A | 5/1990 | Dorn |
| 5,093,474 A | 3/1992 | Grossman et al. |
| 5,104,640 A | 4/1992 | Stokes |
| 5,200,084 A | 4/1993 | Liberti et al. |
| 5,466,574 A | 11/1995 | Liberti et al. |
| 5,512,332 A | 4/1996 | Liberti et al. |
| 5,536,644 A | 7/1996 | Ullman et al. |
| 5,900,361 A | 5/1999 | Klebe |
| 6,013,188 A | 1/2000 | Terstappen et al. |
| 6,602,422 B1 | 8/2003 | Miltenyi et al. |
| 2003/0190760 A1 | 10/2003 | Watkins et al. |
| 2006/0147944 A1 | 7/2006 | Chomczynski |
| 2010/0068690 A1 | 3/2010 | Liotta et al. |
| 2012/0322099 A1 | 12/2012 | Lapen et al. |
| 2013/0345075 A1 | 12/2013 | Espina et al. |
| 2014/0133733 A1 | 5/2014 | Grady et al. |
| 2014/0154689 A1 | 6/2014 | Huang |
| 2014/0295404 A1 | 10/2014 | Goldsborough et al. |
| 2016/0054206 A1 | 2/2016 | Nelson et al. |
| 2017/0029793 A1 | 2/2017 | Hamdan et al. |

FOREIGN PATENT DOCUMENTS

| | | |
|---|---|---|
| CA | 2431683 C | 12/2004 |
| CA | 2532012 C | 3/2005 |
| CA | 2488955 C | 6/2005 |

(Continued)

OTHER PUBLICATIONS

Hong et al. Theranostics vol. 3(6):377-394. (Year: 2013).*
Chen et al. (Scientific Reports vol. 6:16 pages (Year: 2016).*
Bhakdi, Sebastian C. et al. article titled "Easy Employment and Crosstalk-Free Detection of Seven Fluorophores in a Widefield Fluorescence Microscope," Methods and Protoc. 2018, Received: Apr. 25, 2018; Accepted: May 30, 2018; Published: Jun. 1, 2018, doi:10.3390/mps 1020020 (11 pages).

(Continued)

*Primary Examiner* — Lori A. Clow
(74) *Attorney, Agent, or Firm* — Aurora Consulting LLC; Ashley Sloat; Tiffany Miller

(57) ABSTRACT

Disclosed herein are compositions and methods of fixing and staining rare cells. Further, disclosed herein are methods of identifying circulating tumor cells (CTC). In some embodiments, the method includes: imaging a cell sample to identify a cell of interest; determining a first pixel intensity of a stained nuclear area; determining a second pixel intensity of a background area; calculating a ploidy status of the cell of interest by subtracting the second pixel intensity from the first pixel intensity; and determining whether the cell of interest is a CTC based on the ploidy status. The method may be computer implemented, such that the method uses a machine learning algorithm to identify a feature; process the feature to extract a parameter of interest; analyze the parameter of interest; and when the parameter of interest is greater than or less than a pre-determined threshold, classify the cell of interest as a CTC.

11 Claims, 30 Drawing Sheets

(56) References Cited

FOREIGN PATENT DOCUMENTS

| | | | |
|---|---|---|---|
| CA | 2547353 A1 | 7/2005 | |
| CA | 2554138 A1 | 8/2005 | |
| CA | 2554524 A1 | 8/2005 | |
| CA | 2558018 A1 | 10/2005 | |
| DE | 19516323 A1 | 11/1996 | |
| EP | 0176113 A1 | 4/1986 | |
| JP | 2004271497 A | 9/2004 | |
| JP | 2008502913 A | 1/2008 | |
| JP | 2008516189 A | 5/2008 | |
| JP | 2008526226 A | 7/2008 | |
| JP | 2011158365 A | 8/2011 | |
| JP | 2014517324 A | 7/2014 | |
| JP | 2015533210 A | 11/2015 | |
| WO | 2003093795 A2 | 11/2003 | |
| WO | 2006119308 A2 | 11/2006 | |
| WO | 2015093393 A1 | 6/2015 | |

OTHER PUBLICATIONS

Mao Yunxiang et al., "Itereratively training classifiers for circulating tumor cell detection," 2015 IEEE 12th International Symposium on Biomedical Imaging (Isbi), IEEE, Apr. 16, 2015, pp. 190-194.

Sunyoung Park et al., "Morphological Differences between Circulating Tumor Cells from Prostate Cancer Patients and Cultured Prostate Cancer Cells," PLOS ONE ART.N> E85264, vol. 9, No. 1, Jan. 1, 2014, pp. 1-7.

Ammerman, Frank, "A Chrome-Alum Preparations for Delicate and Difficult Fixations," Year. 1950 1 page.

Fagain et al., "Gel-Filtration Chromatography," Springer Science+ Business Media LLC, Methods in Molecular Biology, 2011, p. 25-33, vol. 681.

Felix et al., "Characterization and correlation analysis of pharmaceutical gelatin," Graduate School Theses and Dissertations, University of South Florida, 2003. 164 pages.

Fischer, A., et al., "Fixation and permeabilization of cells and tissues," Cold Spring Harbor Protocol, vol. 3, No. 5, May 1, 2008, p. 1-2, XP008149141.

Frithiof, H., et al., "A novel method for downstream characterization of breast cancer circulating tumor cells following CellSearch isolation," Journal of Translational Medicine, vol. 13, No. 1, Apr. 21, 2015, XP055630721 10 pages.

Kadonaga et al., "Affinity purification of sequence-specific DNA binding proteins," Proceedings of the National Academy of Science, Biochemistry, p. 5889-5893, vol. 83.

Mariod et al., "Review: Gelatin, Source, Extract and Industrial Applications," Acta. Sci. Pol. Technol. Aliment 12(2) 2013, p. 135-147.

Mcneill et al., "Anti-phospholipid antibodies are directed against a complex antigen that includes a lipid-binding Inhibitor of coagulation: B2-Glycoprotein I (apolipoprotein H)," Proceedings of the National Academy of Sciences, Medical Sciences, 1990, p. 4120-4124, vol. 87.

Miltenyi et al., "High Gradient Magnetic Cell Separation with MACS," Wiley-Liss, Inc., Cytometry, 1990, p. 231-238, vol. 11.

Reffle et al., "Critical Capture Radius in Single Wire HGMS," Applied Physics, 1981, p. 225-228, vol. 24, issue 3.

Tagawa et al., "Purification and Partial Characterization of the Major Outer Membrane Protein of Haemophilus somnus," American Society for Microbiology, Infection and Immunity, 1993, p. 91-96, vol. 61, issue 1.

Xu, L., et al., "Optimization and Evaluation of a Novel Size Based Circulating Tumor Cell Isolation System," PLOS ONE, vol. 10, No. 9, Sep. 23, 2015, p. e013832ff, XP055428114 23 pages.

International Search Report of PCT/EP2008/061170, dated May 4, 2009. 3 pages.

International Search Report issued on PCT Application Serial No. PCT/US2017/020905 by ISA/US dated Jul. 3, 2017, p. 1-5.

Written Opinion issued on PCT Application Serial No. PCT/US2017/020905 by ISA/US dated Jul. 3, 2017, p. 1-7.

European Search Report issued on Feb. 24, 2022, on Application No. 21204853.2, 10 pages.

\* cited by examiner

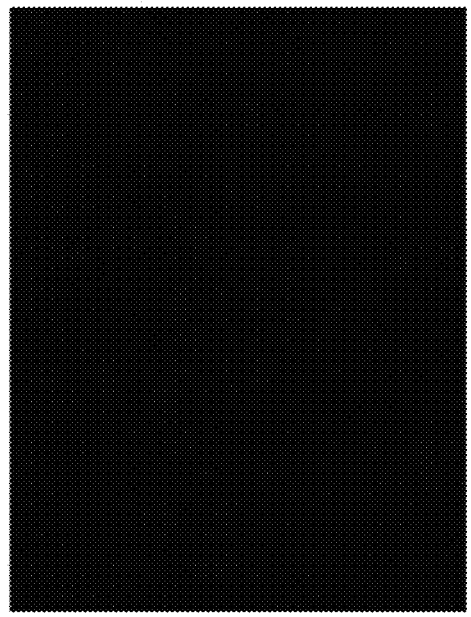
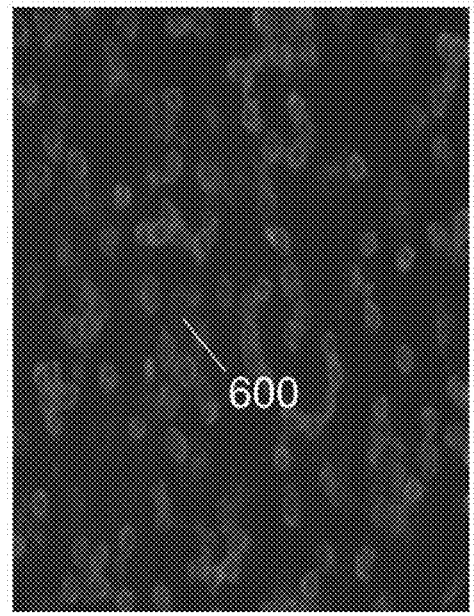
FIG. 13A  FIG. 13B
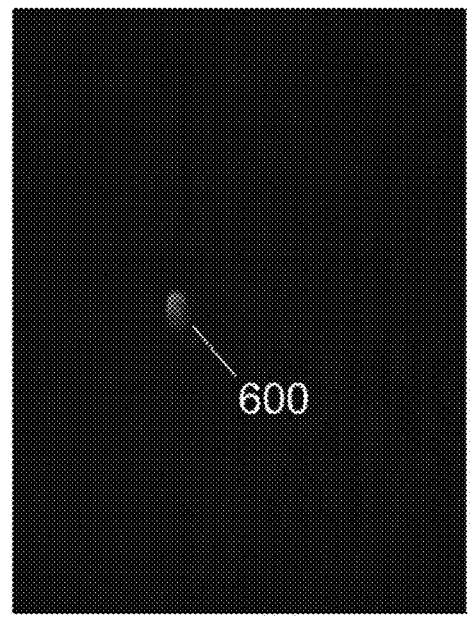
FIG. 13C

SYSTEMS AND METHODS FOR IDENTIFYING RARE CELLS

CROSS-REFERENCE TO RELATED APPLICATIONS

This application is a continuation of the U.S. application Ser. No. 16/083,194, titled "Systems and Methods for Identifying Rare Cells", filed Sep. 7, 2018, which is a U.S. National Stage filing for PCT Application Ser. No. PCT/US17/20905, now published as WO 2017/155869 A1, titled "Compositions and Methods for Identifying Rare Cells", filed Mar. 6, 2017, which claims the priorioty benefit of
  U.S. provisional patent application Ser. No. 62/304,452, titled "Systems and Methods for Fixing Cells," filed Mar. 7, 2016;
  U.S. provisional patent application Ser. No. 62/313,250, titled "Systems, Methods, and Compositions for Fixing and Staining Cells," filed Mar. 25, 2016;
  U.S. provisional patent application Ser. No. 62/313,366, titled "Systems and Methods for Fixing Cells," filed Mar. 25, 2016; and
  U.S. provisional patent application Ser. No. 62/430,542, titled "Compositions and Methods for Identifying Circulating Tumor Cells," filed Dec. 6, 2016, the disclosure of each of which is incorporated by reference in its entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to the fields of molecular biology and microscopy. Described herein are devices, systems, and methods for fixing and staining cells and detecting aneuploidy in cells.

BACKGROUND

Circulating tumor cells (CTCs) are cancerous cells that are shed from the primary tumor and have entered circulation in the vasculature or lymphatics. Some CTCs become embedded in a microenvironment of the body that is conducive to cancer growth, resulting in metastatic cancer. Such metastatic cancer is responsible for 90% of cancer-related deaths (Fidler, I J. (2003) "The pathogenesis of cancer metastasis: the 'seed and soil' hypothesis revisited. Nat Rev Cancer 3, 453-458).

Because of the key role of CTCs in the pathogenesis of metastatic disease, CTCs have become an intense and active area of investigation. Conventionally, CTCs have been identified using physical properties, such as density and cell size, cell-surface related markers, and/or immune properties of the CTC. Unfortunately, such physical properties, cell-surface related markers, and immune properties may also identify healthy cells that do not contribute to disease or fail to detect relevant, pathogenic CTCs. For example, CellSearch™ by Veridex identifies CTC in breast, colorectal, and prostate cancer using positive staining for both epithelial cell adhesion molecule (EpCAM) and cytokeratin. However, when 50 breast cancer cells lines were examined for EpCAM expression, 20% of the cell lines had low levels of EpCAM, suggesting that this 20% would have been missed using the CellSearch™ method (Punnoose et al., (2010) "Molecular biomarker analyses using circulating tumor cells." PLoS One 5, e12517.).

Other methods or techniques for identification and analysis of CTCs have several limitations, for example limited throughput, high frequency of false positives, requires cell permeabilization (rendering the cell useless for most subsequent analysis), dependent on EpCAM (see above), dependent on highly variable markers or properties (e.g., size, density), or the cells are no longer viable at the end of the method.

Further, methods of preparing cells for analysis typically damage the cell and/or tissue and result in the appearance of artifacts, autofluorescent debris or cellular matter, and/or disrupted cellular membranes which can obscure rare cell populations. Such methods use fixatives including cross-linking fixatives (e.g., formaldehyde, paraformaldehyde, etc.) or precipitating fixatives (e.g., ethanol, methanol, etc.). These fixatives also fail to preserve the ribonucleic acid (RNA) of the cells, making subsequent genetic and transcriptome analysis difficult if not impossible.

Additionally, it is often difficult to stain for multiple cellular biomarkers and to clearly distinguish the stained features or biological characteristics from the unstained cellular features. Blocking buffers are commonly used to improve staining specificity, decrease background staining, and improve signal-to-noise ratio. Agents ranging from milk to normal serum to highly purified proteins have been used in blocking buffers to bind free sites on cells and to reduce non-specific binding of antibodies in a stain. However, commonly used blocking buffers are inadequate for rare cells, multi-antibody stains, and stains requiring greater than four fluorophores.

Thus, increasing the ability to analyze and characterize CTCs at a molecular level will enhance cancer screening and therapy, thereby reducing the need for invasive procedures, such as biopsies.

SUMMARY

One aspect of the present disclosure is directed to a reagent system for fixing cells. In some embodiments, the reagent system includes: a first fixing buffer comprising: at least 3% w/v of a first hydrophilic polymer diluted in an alcohol; and a second fixing buffer comprising: at least 5% v/v of a second hydrophilic polymer, at least 0.01% v/v of a detergent, and at least 0.005% w/v of a chrome alum. In some embodiments, the second hydrophilic polymer, detergent, and chrome alum are diluted in saline. In some embodiments, the first fixing buffer is applied to the cells at a temperature colder than −5° C.

Another aspect of the present disclosure is directed to a reagent system for fixing cells. In some embodiments, the reagent system includes: a first fixing buffer comprising: 3% to 20% w/v of a first hydrophilic polymer diluted in an alcohol; and a second fixing buffer comprising: 5% to 30% v/v of a second hydrophilic polymer, 0.01% to 1% v/v of a detergent, and 0.005% to 1% w/v of a chrome alum. In some embodiments, the second hydrophilic polymer, detergent, and chrome alum are diluted in saline. In some embodiments, the first fixing buffer is applied to the cells at a temperature between −90° C. and −5° C.

Another aspect of the present disclosure is directed to a reagent system for fixing cells. In some embodiments, the reagent system includes: a first fixing buffer comprising: 5% w/v of a first hydrophilic polymer diluted in an alcohol; and a second fixing buffer comprising: 15% v/v of a second hydrophilic polymer, 0.4% v/v of a detergent, and 0.01% w/v of a chrome alum. In some embodiments, the second hydrophilic polymer, detergent, and chrome alum are diluted in saline. In some embodiments, the first fixing buffer is applied to the cells at a temperature colder than −15° C.

In some embodiments, the first hydrophilic polymer is one of polyvinylpyrrolidone and glycerol.

In some embodiments, the second hydrophilic polymer is one of glycerol and polyvinylpyrrolidone.

In some embodiments, the alcohol is methanol.

In some embodiments, the detergent is a polysorbate surfactant. In some embodiments, the detergent is polysorbate 20.

In some embodiments, the first and second hydrophilic polymer are the same. In some embodiments, the first and second hydrophilic polymer are different.

Another aspect of the present disclosure is directed to a reagent for fixing a cell. In some embodiments, the reagent includes: at least 3% w/v of a hydrophilic polymer diluted in an alcohol. In some embodiments, the reagent is applied to the cell at a temperature colder than −5° C.

In some embodiments, the cell is a circulating tumor cell. In some embodiments, the cell is embedded in a tissue section.

Another aspect of the present disclosure is directed to a reagent for blocking non-specific binding sites on or in a cell before staining to decrease non-specific staining. In some embodiments, the reagent includes: a hydrophilic polymer; a detergent; and hydrolyzed collagen. In some embodiments, the hydrophilic polymer, detergent, and hydrolyzed collagen are diluted in saline.

Another aspect of the present disclosure is directed to a reagent for blocking non-specific binding sites on or in a cell before staining to decrease non-specific staining. In some embodiments, the reagent includes: at least 1% v/v hydrophilic polymer; at least 0.01% v/v of a detergent; and at least 0.1% w/v hydrolyzed collagen. In some embodiments, the hydrophilic polymer, detergent, and hydrolyzed collagen are diluted in saline.

In some embodiments, the reagent further includes: at least 0.01M Glycine.

Another aspect of the present disclosure is directed to a reagent for blocking non-specific binding sites on or in a cell before staining to decrease non-specific staining. In some embodiments, the reagent includes: 1% to 50% v/v hydrophilic polymer; 0.01% to 2% v/v of a detergent; and 0.1% to 10% w/v hydrolyzed collagen. In some embodiments, the hydrophilic polymer, detergent, and hydrolyzed collagen are diluted in saline.

In some embodiments, the reagent further includes: 0.01M to 1M Glycine.

Another aspect of the present disclosure includes a reagent for blocking non-specific binding sites on or in a cell before staining to decrease non-specific staining. In some embodiments, the reagent includes: 15% v/v hydrophilic polymer; 0.4% v/v of a detergent; and 2% w/v hydrolyzed collagen. In some embodiments, the hydrophilic polymer, detergent, and hydrolyzed collagen are diluted in saline.

In some embodiments, the reagent further includes: 0.3M Glycine.

In some embodiments, the hydrolyzed collagen is pig-derived.

Another aspect of the present disclosure is directed to a method of identifying a cell as a circulating tumor cell. In some embodiments, the method includes: imaging a cell sample to identify a cell of interest; determining a first pixel intensity of a stained nuclear area; determining a second pixel intensity of a background area; calculating a ploidy status of the cell of interest by subtracting the second pixel intensity from the first pixel intensity; and determining whether the cell of interest is a circulating tumor cell based on the ploidy status.

In some embodiments, identifying the cell of interest includes identifying a CD45 negative and Vimentin positive cell.

In some embodiments, the cell sample includes one or more cells.

In some embodiments, the method further includes staining the cell sample with a nuclear stain to identify the stained nuclear area of the cell of interest.

In some embodiments, the background area does not include the cell of interest.

In some embodiments, the cell of interest is determined to be the circulating tumor cell if the ploidy status is less than one. In some embodiments, the cell of interest is determined to be the circulating tumor cell if the ploidy status is greater than two. In some embodiments, the cell of interest is negative for a proliferation marker and is determined to be the circulating tumor cell if the ploidy status is between one and two.

In some embodiments, the method further includes: staining the one or more cells with a vimentin stain and a CD45 stain.

In some embodiments, the nuclear stain is selected from the group consisting of: DRAQ5; 4',6-diamidino-2-phenylindole; propidium iodide; hematoxylin; Kernechtrot dye; Hoechst; and methyl green.

In some embodiments, the method further includes excluding one or more apoptotic cells.

In some embodiments, the method further includes identifying the one or more apoptotic cells by positive staining for Caspase 3.

In some embodiments, the method further includes excluding one or more mitotic cells.

In some embodiments, the method further includes identifying the one or more mitotic cells by positive staining for phosphorylated-histone H3 or Ki-67.

Another aspect of the present disclosure is directed to a computer-implemented method of identifying a cell as a circulating tumor cell. In some embodiments, the method includes: acquiring an image of a cell of interest; identifying a feature associated with the cell of interest, such that the feature includes a nuclear region or marker, a cytoplasmic region or marker, a membrane region or marker, a cellular region or marker, or a combination thereof; processing the feature to extract a parameter of interest, such that the parameter of interest includes a fluorescence intensity, a cell size, a cell shape, a cellular area, a cytoplasmic area, a nuclear area, or a combination thereof; analyzing the parameter of interest; and when the parameter of interest is greater than or less than a pre-determined threshold, classifying the cell of interest as a circulating tumor cell.

In some embodiments, the feature is the nuclear region and the parameter of interest is the fluorescence intensity of the nuclear region.

In some embodiments, the cell of interest is classified as the circulating tumor cell when the parameter of interest is greater than two. In some embodiments, the cell of interest is classified as the circulating tumor cell when the parameter of interest is less than one. In some embodiments, the cell of interest is negative for a proliferation marker and is classified as the circulating tumor cell when the parameter of interest is between one and two.

In some embodiments, the method further includes processing the image to improve a signal-to-noise quality of the image.

In some embodiments, the method further includes staining the cell of interest with a vimentin stain, a CD45 stain, and the nuclear stain.

In some embodiments, the cell of interest is CD45 negative and vimentin positive.

In some embodiments, the nuclear stain is selected from the group consisting of: DRAQ5; 4',6-diamidino-2-phenylindole; propidium iodide; hematoxylin; Kernechtrot dye; Hoechst; and methyl green.

In some embodiments, the method further includes excluding the cell of interest as an apoptotic cell. In some such embodiments, the method may further include identifying the apoptotic cell as Caspase 3 positive.

In some embodiments, the method further includes excluding the cell of interest as a mitotic cell. In some such embodiments, the method may further include identifying the mitotic cell as phosphorylated histone H3 or Ki-67.

In some embodiments, analyzing is performed using machine-learning. In some such embodiments, the machine learning technique comprises: Classification Trees, Discriminant Analysis, k-Nearest Neighbors, Naive Bayes, Support Vector Machines, deep learning, or convolutional neural network.

In some embodiments, the method further includes calculating a confidence score for the classification of the cell of interest.

Another aspect of the present disclosure includes a method for fixing a cell. In some embodiments, the method includes: applying a first fixing buffer to the cell at a temperature colder than −5° C., the first fixing buffer comprising: 3% to 20% w/v of a first hydrophilic polymer diluted in an alcohol; and applying a second fixing buffer to the cell, the second fixing buffer comprising: 5% to 30% v/v of a second hydrophilic polymer, 0.01% to 1% v/v of a detergent, and 0.005% to 1% w/v of a chrome alum. In some embodiments, the second hydrophilic polymer, detergent, and chrome alum are diluted in saline.

In some embodiments, the method further includes applying a blocking buffer to the cell, the blocking buffer comprising: 1% to 50% v/v hydrophilic polymer; 0.01% to 2% v/v of a detergent; and 0.1% to 10% w/v hydrolyzed collagen. In some embodiments, the third hydrophilic polymer, detergent, and hydrolyzed collagen are diluted in saline.

In some embodiments, the first, second, and third hydrophilic polymers are the same. In some embodiments, the first, second, and third hydrophilic polymers are different. In some embodiments, the first, second, and third hydrophilic polymers are one of glycerol and polyvinylpyrrolidone.

In some embodiments, the method further includes cytocentrifuging the cell onto a slide. In some such embodiments, the cell is coated in a buffer comprising: 3% to 30% v/v of the first hydrophilic polymer, and 0.005% to 1% w/v of chrome alum. In some embodiments, the first hydrophilic polymer and chrome alum are diluted in saline.

In some embodiments, the slide is coated with gelatin. In some embodiments, the slide is further coated with chrome alum.

In some embodiments, the cell is a circulating tumor cell. In some embodiments, the cell is embedded in a tissue section.

In some embodiments, the method further includes staining the cell with a fluorophore-tagged antibody.

BRIEF DESCRIPTION OF THE DRAWINGS

The foregoing is a summary, and thus, necessarily limited in detail. The above-mentioned aspects, as well as other aspects, features, and advantages of the present technology described below in connection with various embodiments, with reference made to the accompanying drawings.

FIGS. 5A-8B show experimental results in which A549 cells were stained with anti-cytokeratin phycoerythrin (PE), shown in green.

FIG. 5A shows one example of an experimental result in which cells were cytocentrifuged in a buffer including 0% w/v PVP and 0.01% w/v Chromium Potassium Sulfate diluted in phosphate buffered saline (PBS).

FIG. 7A shows one example of an experimental result in which cells were fixed at room temperature with an intracellular fixative comprising 15% v/v Glycerol and 0.01% w/v Chromium potassium sulfate diluted in PBS.

FIG. 7B shows one example of an experimental result in which cells were fixed on salt ice (e.g., about −2° C.) with an intracellular fixative comprising 15% v/v Glycerol and 0.01% w/v Chromium potassium sulfate diluted in PBS.

FIG. 7C shows one example of an experimental result in which cells were fixed on salt ice (e.g., about −2° C.) with an intracellular fixative comprising 8% v/v Glycerol and 0.01% w/v Chromium potassium sulfate diluted in PBS.

FIG. 7D shows one example of an experimental result in which cells were fixed on salt ice (e.g., about −2° C.) with an intracellular fixative comprising 25% v/v Glycerol and 0.01% w/v Chromium potassium sulfate diluted in PBS.

FIG. 7E shows one example of an experimental result in which cells were fixed on salt ice (e.g., about −2° C.) with an intracellular fixative comprising 15% v/v Glycerol and 0% w/v Chromium potassium sulfate diluted in PBS.

FIG. 7F shows one example of an experimental result in which cells were fixed on salt ice (e.g., about −2° C.) with an intracellular fixative comprising 15% v/v Glycerol and 0.01% w/v Chromium potassium sulfate diluted in PBS.

FIG. 8B shows one example of an experimental result in which cells were blocked with a blocking buffer prior to staining. The blocking buffer included 2% w/v hydrolyzed collagen.

FIG. 13A shows a microscopy image of a BV421-CD14 stain of a prostate cancer cell sample.

FIG. 13B shows a microscopy image of a Pacific Orange-CD45 stain of a prostate cancer cell sample.

FIG. 13C shows a microscopy image of a AlexaFluor488-Vimentin stain of a prostate cancer cell sample.

Figure 1:
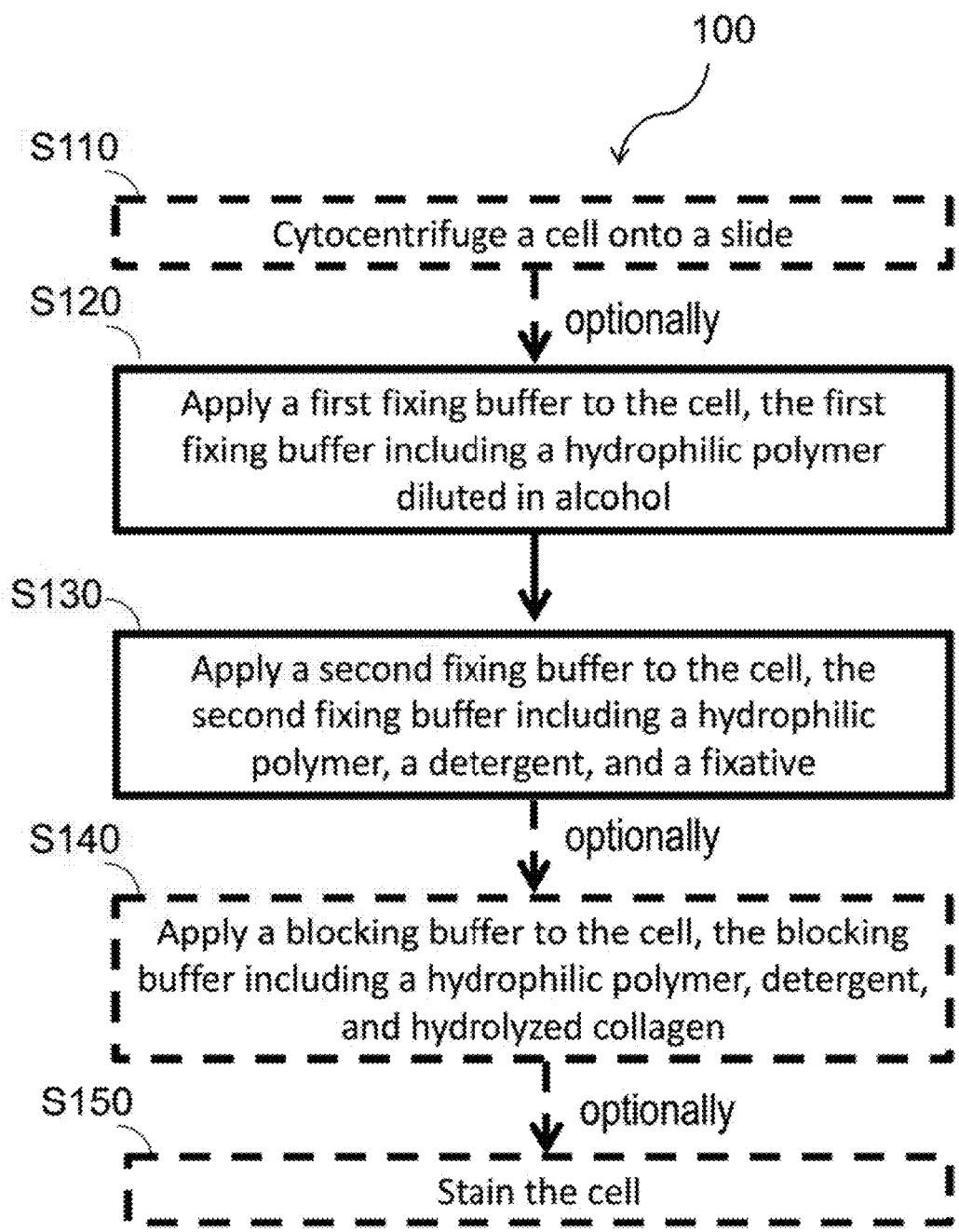
FIG. 1 is a flow chart of one embodiment of a method for fixing a cell.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

As used in the description and claims, the singular form "a", "an" and "the" include both singular and plural references unless the context clearly dictates otherwise. For example, the term "cell" may include, and is contemplated to include, a plurality of cells. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a substance, composition, or method.

As used herein, the term "comprising" or "comprises" is intended to mean that the compositions and methods include the recited elements, and may additionally include any other elements. "Consisting essentially of" shall mean that the compositions and methods include the recited elements and exclude other elements of essential significance to the combination for the stated purpose. Thus, a composition or method consisting essentially of the elements as defined herein would not exclude other materials, features, or steps that do not materially affect the basic and novel characteristic(s) of the claimed disclosure. "Consisting of" shall mean that the compositions and methods include the recited elements and exclude anything more than a trivial or inconsequential element or step. Embodiments defined by each of these transitional terms are within the scope of this disclosure.

In some embodiments, the compositions, methods, and systems described herein are used to fix and/or stain a cell. For example, a cell may include a nucleated cell. In some embodiments, a nucleated cell includes a white blood cell, a precursor of a mature cell, a stem cell, a bone marrow cell, a circulating tumor cell, a cancer cell, a somatic cell, a germline cell, a cell in suspension, a cell adhered to a surface, a cell in a tissue or tissue section, or any other type of cell.

In some embodiments, the cell is fixed with one or more fixatives or fixing buffers. A fixing buffer may include a cross-linking fixative, a precipitating fixative, an oxidizing agent, mercurials, and/or picrates. In some embodiments, the fixative is one or more of methanol, ethanol, propanol, any other alcohol, or two or more alcohols mixed together. For example, two alcohols may be mixed in a ratio ranging from 5%:95% first alcohol:second alcohol to 95%:5% first alcohol:second alcohol. In some embodiments, the fixative is acetone alone or in combination with an alcohol. For example, an alcohol and acetone may be mixed in a ratio ranging from 5%:95% acetone:alcohol to 95%:5% acetone:alcohol.

In some embodiments, the fixative may include a biocompatible moisture preserving agent, hydrophilic polymer, or hygroscopic polymer. For example, the fixative may include glycerol, polyvinylpyrrolidone (PVP), polyethyleneglycol (PEG), dextran, methyl cellulose, polyoxyethylene (POE), gelatin, or any other hygroscopic or hydrophilic polymer.

In some embodiments, one or more reagents, fixatives, or alcohols are diluted in a diluent, phosphate buffered saline (PBS), saline, water, buffered saline, or any other type of biological buffer. In some embodiments, the pH of the diluent is neutral. In some embodiments, the pH is between 6.5 and 8. In one embodiment, the pH is substantially or about 7. In one embodiment, the pH is substantially or about 7.4.

In some embodiments, one or more reagents, fixatives, or alcohols are measured by percent weight/volume (w/v), percent volume/volume (v/v), molarity, percent of total volume or weight, ounces, milliliters, milligrams or grams, or any other unit of measure appropriate for the application.

In some embodiments, a cell may be fixed and/or stained in or on a receptacle. For example, a receptacle may include a test tube, a microtiter plate, a capillary plate, on a slide with or without a coverplate for capillary gap staining, or in any other apparatus or device.

In some embodiments, the receptacle is uncoated, such that the cell is coupled to the surface of the receptacle. In some embodiments, the receptacle is coated, such that coupling of the cell to the receptacle is facilitated by the coating. For example, the coating may include gelatin, poly-L-lysine, collagen, laminin, entactin, heparin sulfate, and/or proteoglycan. In one such embodiment, the receptacle is coated with gelatin. The gelatin may include a fixative, for example chrome alum or chromium (III) salt.

In some embodiments, one or more buffers, fixatives, receptacles, or other components of the invention described herein are sold, commercialized, marketed, advertised, or otherwise packaged individually or bundled together as a reagent system or in a kit. A reagent system or kit may include one or more buffers, fixatives, receptacles for receiving one or more cells, one or more stains, one or more antibodies, and/or any other component for completing all or a portion of the methods described herein.

Disclosed herein are methods for identifying a rare cell in a cell sample. In some embodiments, the rare cell is a circulating tumor cell (CTC). A CTC may include a circulating tumor derived endothelial cell, a tumor-associated macrophage, or other tumor derived or associated cell. The CTC may be identified in a cell sample, for example, but not limited to, a blood sample, a lymph sample, a tissue sample or section, a biopsy sample, or other bodily fluid or tissue sample. The cell sample may include live cells, permeabilized cells, fixed cells, stained cells, or other processed cells types.

Compositions

As described herein, a reagent system or kit for fixing cells includes one or more reagents, buffers, and/or fixatives. A reagent system functions to preserve a cell and/or prepare a cell for staining and/or analysis. In some embodiments, a reagent system includes a first fixing buffer or extracellular fixative. In some embodiments, a reagent system includes a second fixing buffer or an intracellular fixative. In one embodiment, the extracellular fixative and the intracellular fixative are combined into one buffer or reagent. In one embodiment, the extracellular fixative and the intracellular fixative are used separately in succession or substantially simultaneously.

In some embodiments, a reagent system or kit includes an extracellular fixative. The extracellular fixative functions to fix or preserve an exterior surface or extracellular membrane of a cell. The extracellular fixative includes an alcohol or acetone and a hydrophilic or hygroscopic polymer. Examples of alcohols include: methanol, ethanol, propanol, isopropanol, butanol, and pentanol. Examples of hydrophilic or hygroscopic polymers include: glycerol, PVP, PEG, dextran, methyl cellulose, POE, collagen, and gelatin. In some embodiments, the alcohol in the extracellular fixative comprises a mixture of two or more alcohols. In some embodiments, the hydrophilic or hygroscopic polymer comprises a mixture of two or more hydrophilic or hygroscopic polymers.

In some embodiments, the extracellular fixative includes a hydrophilic polymer diluted in alcohol. The hydrophilic polymer functions to preserve moisture in the cell during the fixation process and to improve the integrity of the cell during and after the fixation process. In some embodiments, the extracellular fixative includes at least 3% weight per volume (w/v) of a hydrophilic polymer. In some embodiments, the extracellular fixative includes at least 5% w/v of a hydrophilic polymer. In some embodiments, the extracellular fixative includes 3% to 20% w/v of a hydrophilic polymer. In some embodiments, the extracellular fixative includes 5% to 20% w/v of a hydrophilic polymer. In one embodiment, the extracellular fixative includes 5% w/v of a hydrophilic polymer diluted in an alcohol. In some embodiments, the extracellular fixative includes 1%, 3%, 5%, 10%, 15%, or 20% w/v of a hydrophilic polymer. For example, the hydrophilic polymer may include PVP, glycerol, PEG, or a combination of two or more and the alcohol may include methanol, ethanol, or a combination of both. In some embodiments, the alcohol is replaced with or used in combination with acetone.

In some embodiments, the extracellular fixative is applied to a cell at a temperature colder than or less than −5° C. In some embodiments, the extracellular fixative is applied to a cell at a temperature less than −10° C. In some embodiments, the extracellular fixative is applied to a cell at a temperature less than or equal to −20° C. In some embodiments, the extracellular fixative is applied to a cell at a temperature of −10° C., −60° C., or any temperature therebetween. In some embodiments, the extracellular fixative is applied to a cell at a temperature including or between −15° C. and −30° C. For example, in some embodiments, the extracellular fixative is applied to a cell at a temperature equal to, substantially equal to, or approximately equal to −15° C., −20° C., −25° C., −30° C., −40° C., −50° C., −60° C., −70° C., −80° C., −90° C., −100° C., or −110° C. In one embodiment, the extracellular fixative is applied to a cell at a temperature less than or colder than −15° C. In one embodiment, the extracellular fixative is applied to a cell at a temperature less than or colder than −60° C. In some embodiments, the target temperature or temperature range is achieved by placing the cell or the receptacle comprising the cell on dry ice, in liquid nitrogen, in a freezer tuned to the target temperature, or in a freezing apparatus tuned to the target temperature.

In some embodiments, a reagent system or kit includes an intracellular fixative. The intracellular fixative functions to fix or preserve an intracellular compartment or an intracellular region of a cell and to provide a means, path, or hole through which a stain or antibody can reach an intracellular compartment or region of the cell. The intracellular fixative includes: a hydrophilic or hygroscopic polymer; a detergent, emulsifier, or surfactant; and a fixative. Examples of hydrophilic or hygroscopic polymers include: glycerol, PVP, PEG, dextran, methyl cellulose, POE, collagen, and gelatin. In some embodiments, the hydrophilic or hygroscopic polymer comprises a mixture of two or more hydrophilic or hygroscopic polymers. In some embodiments, the detergent is nonionic, ionic (i.e., cationic or anionic), or zwitterionic. Examples of detergents include: saponin, Triton X-100, Triton X-114, Tween-20 (i.e., polysorbate 20), Tween-40, Tween-80, CHAPS, CHAPSO, and sodium dodecyl sulfate (SDS). Examples of fixatives include: ammonium bichromate, chromium potassium sulfate (i.e., chrome alum), chromic acid, chromyl chloride, potassium chromate, potassium bichromate, carbodiimide (i.e., methanediimine), 1-Ethyl-3-(3-dimethylaminopropyl)carbodiimide (EDC), and carboxymethyl cellulose (CMC).

In some embodiments, the intracellular fixative includes a hydrophilic polymer. In some embodiments, the intracellular fixative includes at least 5% w/v of a hydrophilic polymer diluted in saline, water, phosphate buffered saline, or any buffer solution. In some embodiments, the intracellular fixative includes at least 10% w/v of a hydrophilic polymer. In some embodiments, the intracellular fixative includes at least 15% w/v of a hydrophilic polymer. In some embodiments, the intracellular fixative includes 5% to 30% w/v of a hydrophilic polymer. In some embodiments, the intracellular fixative includes 10% to 30% w/v of a hydrophilic polymer. In some embodiments, the intracellular fixative includes 15% to 30% w/v of a hydrophilic polymer. In some embodiments, the intracellular fixative includes 8%, 15%, 20%, 25%, or 30% w/v of a hydrophilic polymer. In one embodiment, the intracellular fixative includes 15% w/v of a hydrophilic polymer diluted in saline. For example, the hydrophilic polymer may include PVP, glycerol, PEG, or a combination of two or more.

In some embodiments, the intracellular fixative includes a detergent. The detergent functions to puncture holes in the extracellular membrane of the cell to provide a path, means, or route for a buffer, an antibody, or a stain to reach an intracellular compartment or region of the cell. The intracellular fixative includes at least 0.01% volume per volume (v/v) of a detergent diluted in saline, water, phosphate buffered saline, or any buffer solution. In some embodiments, the intracellular fixative includes at least 0.2% v/v of a detergent. In some embodiments, the intracellular fixative includes at least 0.4% v/v of a detergent. In some embodiments, the intracellular fixative includes 0.01% to 1% v/v of a detergent. In some embodiments, the intracellular fixative includes 0.2% to 0.6% v/v of a detergent. In some embodiments, the intracellular fixative includes 0.4% to 1% v/v of a detergent. In one embodiment, the intracellular fixative includes 0.4% v/v of a detergent diluted in saline. In some embodiments, the intracellular fixative includes 0.1%, 0.2%, 0.4%, 0.5%, 0.6%, 0.7%, 0.8%, 0.9%, or 1% v/v of a detergent. For example, the detergent may include Tween-20, Tween-80, Triton X-100, digitonin, saponin, n-dodecyl-β-D-maltoside, any other detergent, or a combination of two or more detergents.

In some embodiments, the intracellular fixative further includes a fixative. The fixative functions to fix or preserve an interior or intracellular region or compartment of the cell. The intracellular fixative includes at least 0.005% w/v of a fixative diluted in saline, water, phosphate buffered saline, or any buffer solution. In some embodiments, the intracellular fixative includes at least 0.008% w/v of a fixative. In some embodiments, the intracellular fixative includes at least 0.01% w/v of a fixative. In some embodiments, the intracellular fixative includes 0.008% to 0.5% w/v of a fixative. In some embodiments, the intracellular fixative includes 0.01% to 0.1% w/v of a fixative. In one embodiment, the intracellular fixative includes 0.01% w/v of a fixative diluted in saline. In some embodiments, the intracellular fixative includes 0.005%, 0.006%, 0.007%, 0.008%, 0.009%, 0.01%, 0.2%, 0.3%, 0.4%, or 0.5% w/v of a fixative. For example, the fixative may include: ammonium bichromate, chromium potassium sulfate (i.e., chrome alum), chromyl chloride, potassium chromate, potassium bichromate, carbodiimide (i.e., methanediimine), EDC, CMC, or a combination of two or more fixatives.

In some embodiments, the intracellular fixative is applied to a cell at a temperature less than freezing temperature (e.g., less than 0° C.). In some embodiments, the intracellular fixative is applied to a cell at a temperature colder than or less than 1° C. In some embodiments, the intracellular fixative is applied to a cell at a temperature including or between 0° C. and −10° C. In some embodiments, the intracellular fixative is applied to a cell at a temperature including or between 1° C. and −5° C. In one embodiment, the intracellular fixative is applied to a cell at a temperature substantially equal to or about 0° C. In some embodiments, the intracellular fixative is applied to a cell at −5° C., −4° C., −3° C., −2° C., −1° C., 0° C., or 1° C. In some embodiments, the target temperature or temperature range is achieved by placing the cell or the receptacle comprising the cell on ice, on salt ice, in a freezer tuned to the target temperature, or in a chilling apparatus tuned to the target temperature.

In some embodiments, the hydrophilic polymer used in the extracellular fixative is the same as the hydrophilic polymer used in the intracellular fixative. In some embodiments, the hydrophilic polymer used in the extracellular fixative is different than the hydrophilic polymer used in the intracellular fixative.

In some embodiments, a reagent system or kit includes a blocking buffer. The blocking buffer functions to block or bind non-specific antibody or stain binding sites on the surface of or in the cell. The blocking buffer includes a hydrophilic polymer, a detergent, and hydrolyzed collagen diluted in saline, water, phosphate buffered saline, or any buffer solution.

In some embodiments, the blocking buffer includes at least 1% w/v of a hydrophilic polymer diluted in saline, water, phosphate buffered saline, or any buffer solution. In some embodiments, the blocking buffer includes at least 10% w/v of a hydrophilic polymer. In some embodiments, the blocking buffer includes at least 20% w/v of a hydrophilic polymer. In some embodiments, the blocking buffer includes at least 30% w/v of a hydrophilic polymer. In some embodiments, the blocking buffer includes 1% to 50% w/v of a hydrophilic polymer. In some embodiments, the blocking buffer includes 10% to 45% w/v of a hydrophilic. In some embodiments, the blocking buffer includes 20% to 40% w/v of a hydrophilic polymer. In one embodiment, the blocking buffer includes 30% w/v of a hydrophilic polymer diluted in saline. In some embodiments, the blocking buffer includes 5%, 10%, 15%, 20%, 25%, 30%, 35%, 40%, 45%, or 50% w/v of a hydrophilic polymer. For example, the hydrophilic polymer may include PVP, glycerol, PEG, or a combination of two or more.

In some embodiments, the blocking buffer includes a detergent. In some embodiments, the blocking buffer includes at least 0.01% v/v of a detergent diluted in saline, water, phosphate buffered saline, or any buffer solution. In some embodiments, the blocking buffer includes at least 0.2% v/v of a detergent. In some embodiments, the blocking buffer includes at least 0.4% v/v of a detergent. In some embodiments, the blocking buffer includes 0.01% to 1% v/v of a detergent. In some embodiments, the blocking buffer includes 0.2% to 0.6% v/v of a detergent. In some embodiments, the blocking buffer includes 0.4% to 1% v/v of a detergent. In one embodiment, the blocking buffer includes 0.4% v/v of a detergent diluted in saline. In some embodiments, the blocking buffer includes 0.01%, 0.1%, 0.2%, 0.3%, 0.4%, 0.5%, 0.6%, 0.7%, 0.8%, 0.9%, or 1% v/v of a detergent. For example, the detergent may include Tween-20, Tween-80, Triton X-100, digitonin, saponin, n-dodecyl-β-D-maltoside, any other detergent, or a combination of two or more detergents.

In some embodiments, the blocking buffer includes hydrolyzed collagen. The hydrolyzed collagen functions as a protein with affinity for or capable of binding non-specific antibody or stain binding sites on an extracellular surface of a cell or intracellularly. In some embodiments, the blocking buffer includes at least 0.1% w/v hydrolyzed collagen. In some embodiments, the blocking buffer includes at least 0.5% w/v hydrolyzed collagen. In some embodiments, the blocking buffer includes at least 1% w/v hydrolyzed collagen. In some embodiments, the blocking buffer includes at least 2% w/v hydrolyzed collagen. In some embodiments, the blocking buffer includes 0.1% to 10% w/v hydrolyzed collagen. In some embodiments, the blocking buffer includes 0.5% to 5% w/v hydrolyzed collagen. In some embodiments, the blocking buffer includes 1% to 3% w/v hydrolyzed collagen. In one embodiment, the blocking buffer includes 2% w/v hydrolyzed collagen diluted in saline. In some embodiments, the blocking buffer includes 0.1%, 0.2%, 0.3%, 0.4%, 0.5%, 0.6%, 0.7%, 0.8%, 0.9%, 1%, 1.25%, 1.5%, 1.75%, 2%, 2.25%, 2.5%, 2.75%, or 3% w/v of hydrolyzed collagen. In some embodiments, the hydrolyzed collagen is derived from an animal source. In one embodiment, the hydrolyzed collagen is pig or porcine-derived. In one embodiment, the hydrolyzed collagen is cow or bovine-derived. In one embodiment, the hydrolyzed collagen is fish-derived.

In some embodiments, the blocking buffer includes glycine. Glycine functions to bind free aldehyde groups in proteins that would otherwise bind antibodies or stain resulting in increased background or artifacts. In some embodiments, the blocking buffer includes at least 0.01M glycine. In some embodiments, the blocking buffer includes at least 0.1M glycine. In some embodiments, the blocking buffer includes at least 0.3M glycine. In some embodiments, the blocking buffer includes 0.01M to 1M glycine. In some embodiments, the blocking buffer includes 0.1M to 0.5M glycine. In one embodiment, the blocking buffer includes 0.3M glycine. In some embodiments, the blocking buffer includes 0.01M, 0.05M, 0.1M, 0.15M, 0.2M, 0.25M, 0.3M, 0.35M, 0.4M, 0.45M, or 0.5M glycine.

In some embodiments, a reagent system or kit includes a cytocentrifugation buffer. The cytocentrifugation buffer functions to protect the cell and/or provide a vehicle through which the cell is applied to a receptacle, for example using a cytocentrifuge. The cytocentrifugation buffer includes a hydrophilic polymer and a fixative diluted in saline, water, phosphate buffered saline, or any buffer solution.

In some embodiments, the cytocentrifugation buffer includes at least 3% w/v of a hydrophilic polymer. In some embodiments, the cytocentrifugation buffer includes at least 5% w/v of a hydrophilic polymer. In some embodiments, the cytocentrifugation buffer includes at least 10% w/v of a hydrophilic polymer. In some embodiments, the cytocentrifugation buffer includes 1% to 20% w/v of a hydrophilic polymer. In some embodiments, the cytocentrifugation buffer includes 5% to 15% w/v of a hydrophilic polymer. In one embodiment, the cytocentrifugation buffer includes 10% w/v of a hydrophilic polymer diluted in saline. In some embodiments, the cytocentrifugation buffer includes 1%, 3%, 5%, 7%, 9%, 10%, 12%, 15%, 17%, or 20% w/v of a hydrophilic polymer.

In some embodiments, the cytocentrifugation buffer includes at least 0.005% w/v of a fixative diluted in saline, water, phosphate buffered saline, or any buffer solution. In some embodiments, the cytocentrifugation buffer includes at least 0.008% w/v of a fixative. In some embodiments, the cytocentrifugation buffer includes at least 0.01% w/v of a fixative. In some embodiments, cytocentrifugation buffer includes 0.008% to 0.5% w/v of a fixative. In some embodiments, the cytocentrifugation buffer includes 0.01% to 0.1% w/v of a fixative. In one embodiment, the cytocentrifugation buffer includes 0.01% w/v of a fixative diluted in saline. In some embodiments, the cytocentrifugation buffer includes 0.0005%, 0.008%, 0.01%, 0.05%, 0.2%, 0.25%, 0.3%, 0.35%, 0.4%, 0.45%, or 0.5% w/v of a fixative. For example, the fixative may include: ammonium bichromate, chromium potassium sulfate (i.e., chrome alum), chromyl chloride, potassium chromate, potassium bichromate, carbodiimide (i.e., methanediimine), EDC, and CMC.

In some embodiments, a reagent system or kit includes an antibody binding buffer. The antibody binding buffer functions to improve or promote antibody or stain binding to an extracellular or intracellular surface of a cell. The antibody binding buffer includes a hydrophilic polymer and a detergent.

In some embodiments, the antibody binding buffer includes at least 5% w/v of a hydrophilic polymer diluted in saline, water, phosphate buffered saline, or any buffer solution. In some embodiments, the antibody binding buffer includes at least 10% w/v of a hydrophilic polymer. In some embodiments, the antibody binding buffer includes at least 15% w/v of a hydrophilic polymer. In some embodiments, the antibody binding buffer includes 5% to 30% w/v of a hydrophilic polymer. In some embodiments, the antibody binding buffer includes 10% to 30% w/v of a hydrophilic polymer. In some embodiments, the antibody binding buffer includes 15% to 30% w/v of a hydrophilic polymer. In one embodiment, the antibody binding buffer includes 15% w/v of a hydrophilic polymer diluted in saline. In some embodiments, the antibody binding buffer includes 5%, 10%, 15%, 20%, 25%, 30%, 35%, or 40% w/v of a hydrophilic polymer. For example, the hydrophilic polymer may include PVP, glycerol, PEG, or a combination of two or more.

In some embodiments, the antibody binding buffer includes a detergent. In some embodiments, the antibody binding buffer includes at least 0.01% v/v of a detergent diluted in saline, water, phosphate buffered saline, or any buffer solution. In some embodiments, the antibody binding buffer includes at least 0.2% v/v of a detergent. In some embodiments, the antibody binding buffer includes at least 0.4% v/v of a detergent. In some embodiments, the antibody binding buffer includes 0.01% to 1% v/v of a detergent. In some embodiments, the antibody binding buffer includes 0.2% to 0.6% v/v of a detergent. In some embodiments, the antibody binding buffer includes 0.4% to 1% v/v of a detergent. In one embodiment, the antibody binding buffer includes 0.4% v/v of a detergent diluted in saline. In some embodiments, the antibody binding buffer includes, 0.01%, 0.1%, 0.2%, 0.3%, 0.4%, 0.5%, 0.6%, 0.7%, 0.8%, 0.9%, or 1% v/v of a detergent. For example, the detergent may include Tween-20, Tween-80, Triton X-100, digitonin, saponin, n-dodecyl-β-D-maltoside, any other detergent, or a combination of two or more detergents.

In some embodiments, a reagent system or kit includes one or more receptacles, for example a slide, for fixing, staining, viewing, and/or analyzing a cell. The one or more receptacles may be coated with gelatin, collagen, or another cell-binding reagent to improve or promote adherence of the cell to a surface of the receptacle. Examples of gelatin include: Type A (i.e., derived from acid-cured tissue) and Type B (i.e., derived from lime-cured tissue). In some embodiments, the gelatin includes a cationic reagent. Examples of cationic reagents include: chromium potassium sulfate dodecahydrate, ammonium bichromate, chromium potassium sulfate (i.e., chrome alum), chromyl chloride, potassium chromate, potassium bichromate, carbodiimide (i.e., methanediimine), EDC, and CMC. The cationic reagent functions to positively charge the receptacle to improve attraction and adherence of negatively charged cells and/or tissue sections to the receptacle.

In some embodiments, a reagent system or kit includes a receptacle cleaning buffer. The receptacle cleaning buffer functions to remove debris and/or autofluorescent particles from one or more surfaces of the receptacle. In some embodiments, the receptacle cleaning buffer includes a ratio of alcohol to acid. Examples of alcohols include: methanol, ethanol, propanol, isopropanol, butanol, and pentanol. Examples of acids include: hydrochloric acid, acetic acid, hydrofluoric acid, hydrobromic acid, and hydroiodic acid. In some embodiments, the ratio of alcohol to acid is 5%:95%; 10%:90%; 15%:85%; 20%:80%; 25%:75%; 30%:70%; 35%:65%; 40%:60%; 45%:55%; 50%:50%; 55%:45%; 60%:40%; 65%:35%; 70%:30%; 75%:25%; 80%:20%; 85%:15%; 90%:10%; or 95%:5%. In one embodiment, the ratio of alcohol to acid is 50%:50%. In one embodiment, the ratio of alcohol to acid is 40%:60%. In one embodiment, the ratio of alcohol to acid is 60%:40%.

Methods

As shown in FIG. 1, a method 100 for fixing a cell includes: applying a first fixing buffer to the cell, the first fixing buffer including a hydrophilic polymer diluted in alcohol S110; and applying a second fixing buffer to the cell, the second fixing buffer including a hydrophilic polymer, detergent, and hydrolyzed collagen S120. The method functions to fix or preserve a cell for staining, viewing, and/or analysis.

In some embodiments, applying a first fixing buffer to the cell, as recited at S120, involves applying the first fixing buffer or extracellular fixative to the cell at a temperature colder than or less than −5° C. In some embodiments, the first fixing buffer or extracellular fixative is applied to the cell at a temperature less than −10° C. In some embodiments, the extracellular fixative is applied to the cell at a temperature less than −15° C. In some embodiments, the extracellular fixative is applied to the cell at a temperature less than −20° C. In some embodiments, the extracellular fixative is applied to the cell at a temperature less than −30° C. In some embodiments, the extracellular fixative is applied to the cell at a temperature less than −40° C. In some embodiments, the extracellular fixative is applied to the cell at a temperature less than −50° C. In some embodiments, the extracellular fixative is applied to the cell at a temperature less than −60° C. The sub-freezing temperature in combination with the hydrophilic polymer functions to preserve the integrity of the cell and reduce artifacts or autofluorescent features associated with the cell. In some embodiments, block S120 includes incubating the cell with the extracellular fixative. In some embodiments, the incubation period is at least five minutes. In some embodiments, the incubation period is at least ten minutes. In some embodiments, the incubation period is at least fifteen minutes. In one embodiment, the incubation period is fifteen minutes. In some embodiments, the incubation period is between five minutes and thirty minutes.

At block S130, applying a second fixing buffer to the cell may include applying the second fixing buffer or intracellular fixative to the cell at a temperature colder than or less than 4° C. In some embodiments, the intracellular fixative is applied to the cell at a temperature less than 1° C. In some embodiments, the intracellular fixative is applied to the cell at a temperature less than 0° C. In some embodiments, the intracellular fixative is applied to the cell at a temperature less than −2° C. The freezing temperature in combination with the hydrophilic polymer functions to preserve the integrity of the cell and reduce artifacts or autofluorescent features associated with the cell. In some embodiments, block S130 includes incubating the cell in the intracellular fixative. In some embodiments, the incubation period is at least twenty minutes. In some embodiments, the incubation period is at least thirty minutes. In some embodiments, the incubation period is at least sixty minutes. In some embodiments, the incubation period is at least 120 minutes. In some embodiments, the incubation period is at least 180 minutes. In some embodiments, the incubation period is at least 240 minutes. In one embodiment, the incubation period is thirty minutes. In some embodiments, the incubation period is between fifteen minutes and 300 minutes.

In some embodiments, the method 100 optionally includes block S110, which recites cytocentrifuging a cell onto a slide. Block S110 functions to couple or adhere the cell to a receptacle for further processing and/or analysis. The slide or receptacle may be coated with a substance or reagent, for example a cationic substance, collagen, or gelatin. In some embodiments, block S110 includes cleaning the receptacle or slide prior to cytocentrifuging the cell onto the slide or receptacle. The slide or receptacle may be cleaned with a receptacle cleaning buffer, as described elsewhere herein. In some embodiments, block S110 includes suspending the cell in a cytocentrifugation buffer, as described elsewhere herein, before cytocentrifugation. In some embodiments, block S110 includes allowing the receptacle or slide to dry after cytocentrifugation to remove excess cytocentrifugation buffer from the surface of the receptacle or slide.

In some embodiments, the method 100 optionally includes block S140, which recites applying a blocking buffer to the cell, the blocking buffer, as described elsewhere herein, including a hydrophilic polymer, detergent, and hydrolyzed collagen. Block S140 functions to reduce non-specific antibody or stain binding by saturating non-specific binding sites with an irrelevant protein (e.g., hydrolyzed collagen). In some embodiments, block S140 includes incubating the cell with the blocking buffer for a defined time period at a defined temperature. In some embodiments, the time period is at least thirty minutes. In some embodiments, the time period is at least forty-five minutes. In some embodiments, the time period is at least sixty minutes. In some embodiments, the time period is thirty to ninety minutes. In some embodiments, the time period is forty-five to seventy-five minutes. In one embodiment, the time period is sixty minutes. In some embodiments, the defined temperature is colder than 5° C. In some embodiments, the defined temperature is colder than 4° C. In some embodiments, the defined temperature is colder than 2° C. In some embodiments, the defined temperature is colder than 0° C. In some embodiments, the defined temperature range is −5° C. to 5° C. In some embodiments, the defined temperature range is 0° C. to 4° C. In one embodiment, the defined temperature is about or substantially −2° C.

In some embodiments, the method 100 optionally includes block S150, which recites staining the cell. Block S150 functions to highlight or contrast different features or regions of the cell. In some embodiments, staining includes: immunofluorescence staining, immunohistochemistry, in situ hybridization, or any other staining technique. In some embodiments, staining includes tagging a cell with an unlabeled or protein-conjugated (e.g., biotin) primary antibody that recognizes a protein or nucleic acid of interest and labeling the primary antibody with a labeled (e.g., fluorophore) or enzymatically-active (e.g., streptavidin) secondary antibody that recognizes the primary antibody. In some embodiments, staining includes labeling the cell with a labeled primary antibody that recognizes a protein or nucleic acid of interest. The label may include: a fluorophore, an enzyme (e.g., streptavidin, horseradish peroxidase, etc.), a bioluminescent molecule, or any other type of label that can be visualized microscopically. In some embodiments, staining the cell occurs at a temperature of less than 0° C. In some embodiments, staining the cell occurs at a temperature of less than −1° C. In some embodiments, staining the cell occurs at a temperature of less than −2° C. In some embodiments, staining the cell occurs at a temperature of less than −3° C. In some embodiments, staining the cell occurs at substantially −2° C., −3° C., or a temperature there between.

Figure 2:
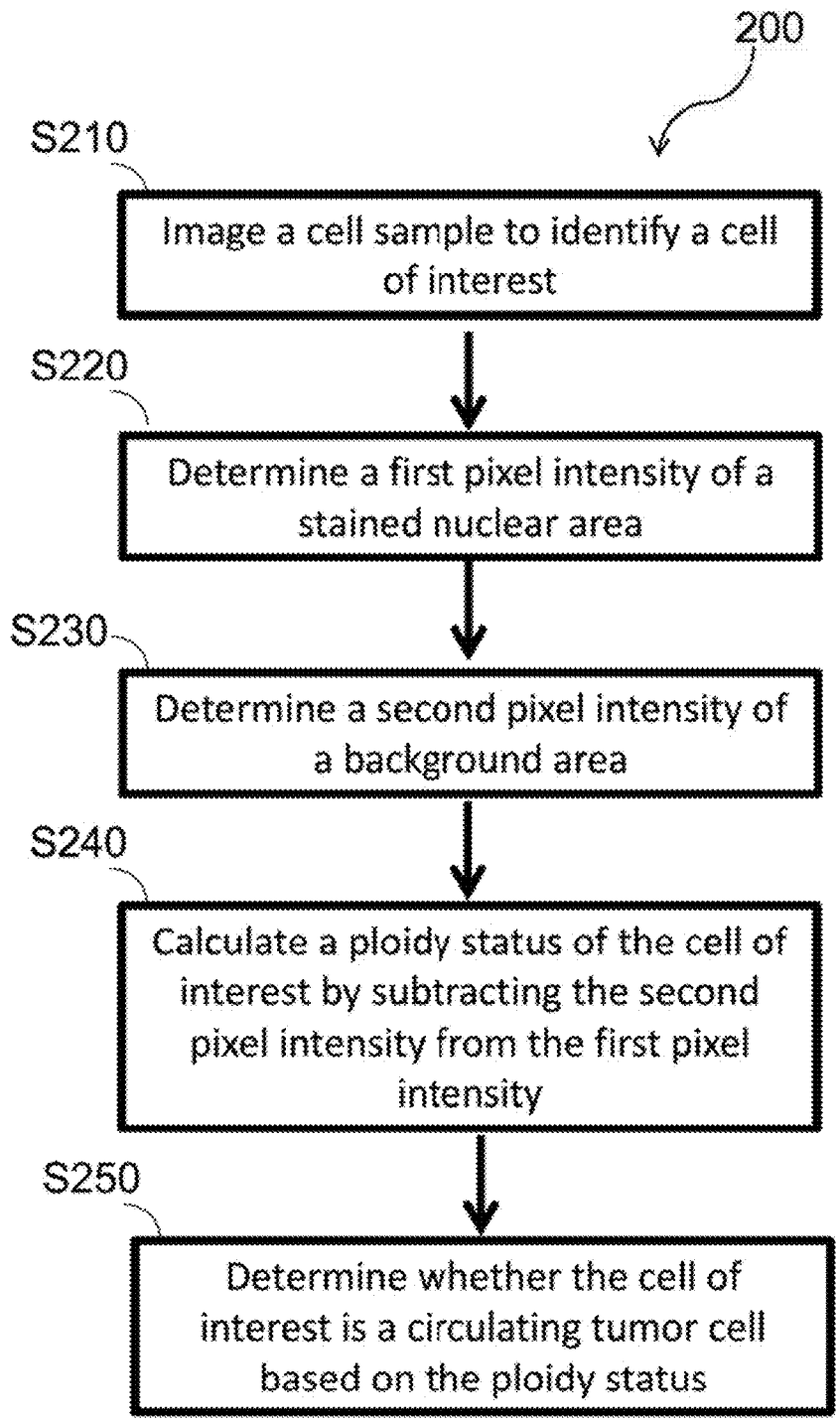
FIG. 2 is a flow chart of one embodiment of a method of identifying a cell as a circulating tumor cell.

As shown in FIG. 2, a method 200 of identifying a cell as a circulating tumor cell of one embodiment includes imaging a cell sample to identify a cell of interest in block S210; determining a first pixel intensity of a stained nuclear area in block S220; determining a second pixel intensity of a background area in block S230; calculating a ploidy status of the cell of interest by subtracting the second pixel intensity from the first pixel intensity in block S240; and determining whether the cell of interest is a circulating tumor cell based on the ploidy status in block S250. The method functions to determine a pixel intensity or fluorescence intensity of a stained area in order to determine if the cell is euploidic, aneuploidic, hyperploidic, hypoploidic, or otherwise has an abnormal DNA content. In some embodiments, the method functions to identify a circulating tumor cell in a cell sample. The method is used in the cancer biology field but can additionally or alternatively be used in microscopy, cellular analysis, cell cycle studies or for any other suitable applications, for example investigational or teaching applications.

As shown in FIG. 2, one embodiment of a method 200 of identifying a cell as a circulating tumor cell includes block S210, which recites imaging a cell sample to identify a cell of interest. Block S210 functions to microscopically view one or more cells in a cell sample in order to process the image to identify a cell of interest. In some embodiments, the method includes staining the cell sample with one or more stains, antibodies, DNA-incorporating dyes, either directly or indirectly (e.g., using secondary antibodies), and either or both intracellularly or extracellularly. Staining the cell sample may include highlighting one or more markers of interest on a cell of interest or highlighting one or more cells for exclusion from the analysis. In one such embodiment, the method includes staining the cell sample with a nuclear stain to identify a stained nuclear area of the cell of interest. Non-limiting examples of nuclear stains include: DRAQ5, propidium iodide (PI), 4',6-diamidino-2-phenylindole (DAPI); hematoxylin; Kernechtrot dye; Hoechst;

methyl green, other nuclear dye exhibiting stoichiometric DNA binding, or any combination thereof. Further in some embodiments, identifying a cell of interest includes identifying a CD45 negative cell, a Vimentin positive cell, an EpCAM positive cell, an EpCAM negative cell, a phosphorylated serine 10 Histone H3 negative cell, a nuclear proliferation marker negative cell, a Ki-67 negative cell, a Caspase 3 negative cell, an apoptosis marker negative cell, a CD14 negative cell, a CD34 positive cell, a CD34 negative cell, or any combination thereof. In some embodiments, the method includes excluding one or more apoptotic, necrotic, mitotic, or other cells, for example undergoing a normal or healthy process of cellular death or DNA multiplication or one or more cells not exhibiting other markers indicative of cancer or cancerous transformation.

As shown in FIG. 2, one embodiment of a method 200 of identifying a cell as a circulating tumor cell includes block S220, which recites determining a first pixel intensity of a stained nuclear area. Block S220 functions to manually or automatically identify a stained nuclear area and determine a pixel intensity of said stained nuclear area. In some embodiments, the method includes identifying a first perimeter of a stained nuclear area (i.e., a nuclear perimeter), such that the first pixel intensity is derived by measuring a pixel intensity of an area contained by the perimeter. In some such embodiments, the method includes multiplying the area defined by the nuclear perimeter by the first pixel intensity. In some embodiments, the method includes identifying a second perimeter, said second perimeter identifying a cell membrane of a cell (i.e., membrane perimeter), for example to determine a cell size. In one such embodiment, the method includes comparing the first perimeter to the second perimeter to determine a nuclear area, cytoplasmic area, a total cell area, or ratio therebetween.

As shown in FIG. 2, one embodiment of a method 200 of identifying a cell as a circulating tumor cell includes block S230, which recites determining a second pixel intensity of a background area. Block S230 functions to manually or automatically identify a background area and determine a pixel intensity of said background area. In some embodiments, the background area comprises a plurality of background areas. In some embodiments, the method includes defining a background area, said background area being devoid of cells or other cellular matter, but may include non-specific staining or background staining. Further, the method may include defining a perimeter around the background area, said perimeter being called a background perimeter. As such, the method may include multiplying an area defined by the background perimeter by the second pixel intensity of the background area.

As shown in FIG. 2, one embodiment of a method 200 of identifying a cell as a circulating tumor cell includes block S240, which recites calculating a ploidy status of the cell of interest by subtracting the second pixel intensity from the first pixel intensity. Block S240 functions to remove non-specific or background staining pixel intensity from the first pixel intensity by subtracting the second pixel intensity derived from the background from the first pixel intensity. In some embodiments, the ploidy status is one or substantially one, indicating normal or a healthy amount of DNA. In some embodiments, the ploidy status is less than one, indicating an apoptotic or necrotic cell or a cancerous cell that includes an abnormally low amount of DNA. In some embodiments, the ploidy status is greater than two, indicating a cancerous cell that includes an abnormally high amount of DNA. In some embodiments, the ploidy status is between one and two or is exactly two. In some such embodiments, if the cell is negative for a proliferation or mitosis marker, the cell is likely a cancerous cell that includes an abnormally high amount of DNA. Alternatively, in some such embodiments, if the cell is positive for a proliferation or mitosis marker, the cell is likely a cell progressing through mitosis. In some embodiments, the method includes reducing a likelihood that the cell is apoptotic or necrotic by counterstaining the cell with an apoptosis marker, for example Caspase 3. In some embodiments, the method includes reducing a likelihood that the cell is mitotic by counterstaining the cell with a proliferation or mitosis marker, for example Ki-67 or phosphorylated serine 10 Histone H3.

As shown in FIG. 2, one embodiment of a method 200 of identifying a cell as a circulating tumor cell includes block S250, which recites determining whether the cell of interest is a circulating tumor cell based on the ploidy status. In some embodiments, the method includes identifying the cell of interest as a circulating tumor cell if the ploidy status is less than one. In some embodiments, the method includes identifying the cell of interest as a circulating tumor cell if the ploidy status is greater than two. In some embodiments, the method includes identifying the cell of interest as a circulating tumor cell if the cell is negative for a proliferation or mitosis marker and if the cell has a ploidy status between one and two.

In some embodiments, the method includes fixing the cell sample or the cell of interest using the compositions and methods described elsewhere herein.

In some embodiments, the method includes processing or lysing the cell of interest to extract DNA, RNA, or protein. In some embodiments, the method includes processing or analyzing the cell to identify a tissue, cancer, tumor, location, environment, or lineage of origin.

In some embodiments, the method includes diagnosing a patient with a condition based on an identity of the cell of interest.

Figure 3:
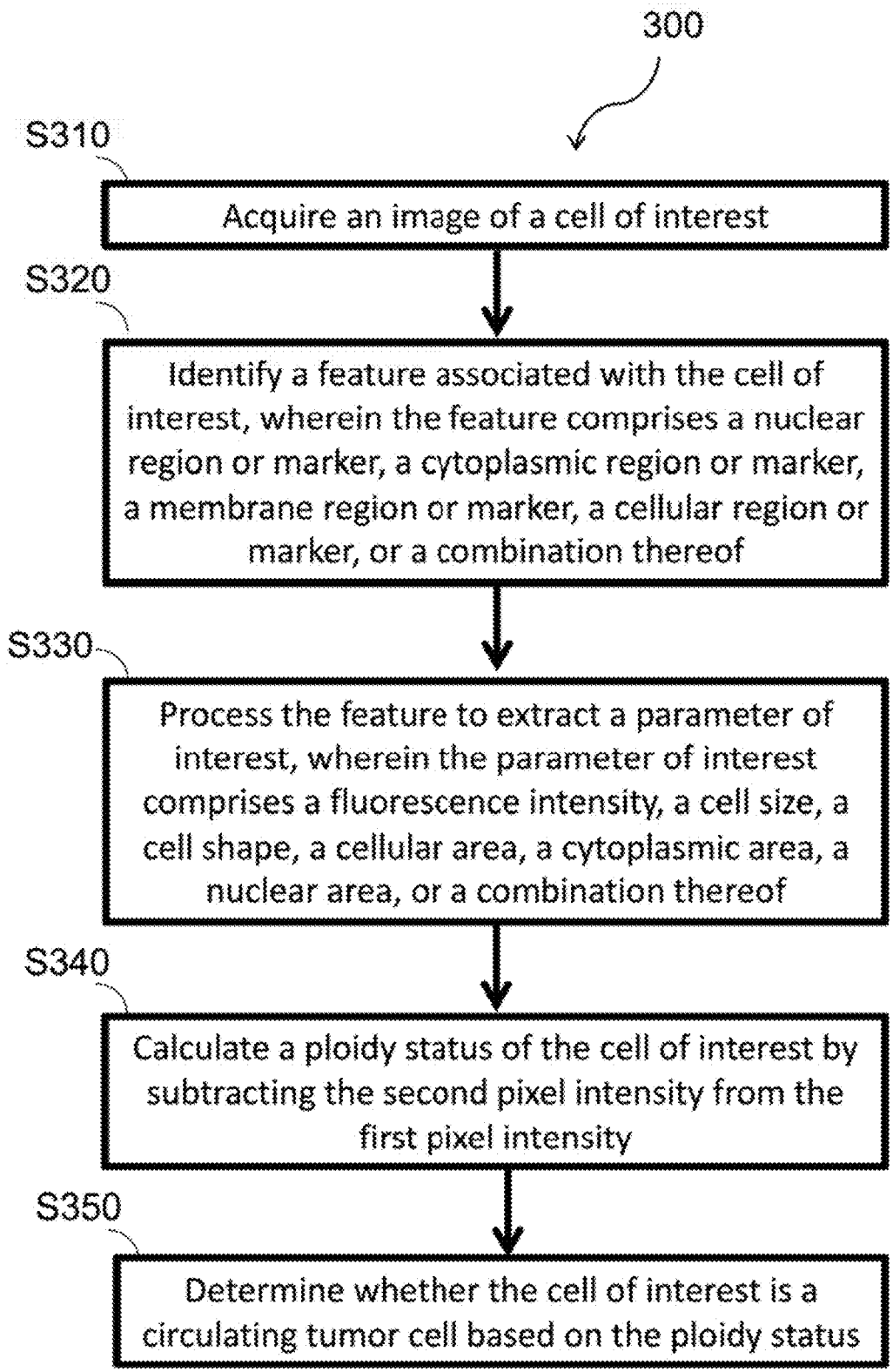
FIG. 3 is a flow chart of one embodiment of a computer-implemented method of identifying a cell as a circulating tumor cell.

As shown in FIG. 3, a computer-implemented method 300 of identifying a cell as a circulating tumor cell of one embodiment includes acquiring an image of a cell of interest in block S310; identifying a feature associated with the cell of interest, such that the feature comprises a nuclear region or marker, a cytoplasmic region or marker, a membrane region or marker, a cellular region or marker, or a combination thereof in block S320; processing the feature to extract a parameter of interest, such that the parameter of interest comprises a fluorescence intensity, a cell size, a cell shape, a cellular area, a cytoplasmic area, a nuclear area, or a combination thereof in block S330; analyzing the parameter of interest in block S340; and when the parameter of interest is greater than or less than a pre-determined threshold, classifying the cell of interest as a circulating tumor cell in block S350. The method functions to automatically identify a cell of interest in a cell sample as being euploidic, aneuploidic, hyperploidic, hypoploidic, or otherwise having an abnormal DNA content. In some embodiments, the method functions to identify a circulating tumor cell in a cell sample. The method is used in the cancer biology field but can additionally or alternatively be used in microscopy, cellular analysis, cell cycle studies or for any other suitable applications, for example investigational or teaching applications.

As shown in FIG. 3, one embodiment of a computer-implemented method 300 of identifying a cell as a circulating tumor cell includes block S310, which recites acquiring an image of a cell of interest. Non-limiting examples of types of images include: microscopy images, confocal images, fluorescence images, flow cytometry images, or another type of image.

As shown in FIG. 3, one embodiment of a computer-implemented method 300 of identifying a cell as a circulating tumor cell includes block S320, which recites identifying a feature associated with the cell of interest, such that the feature comprises a nuclear region or marker, a cytoplasmic region or marker, a membrane region or marker, a cellular region or marker, or a combination thereof. In some embodiments, the feature is identified based on the absence of or negative staining of a cellular region or marker or other cellular characteristic; in other embodiments, the feature is identified based on the presence of or positive staining of a cellular marker or other cellular characteristic. In some embodiments, identifying a feature includes measuring a pixel intensity; determining a location of staining; identifying a nuclear region, for example based on staining or location; identifying a cytoplasmic region, for example based on staining or location; processing the image to reduce noise or enhance contrast; or other method or process. In some embodiments, identifying a feature includes using image recognition.

As shown in FIG. 3, one embodiment of a computer-implemented method 300 of identifying a cell as a circulating tumor cell includes block S330, which recites processing the feature to extract a parameter of interest, such that the parameter of interest comprises a fluorescence intensity, a cell size, a cell shape, a cellular area, a cytoplasmic area, a nuclear area, or a combination thereof. In some embodiments, the feature is the nuclear region and the parameter of interest is the fluorescence intensity of the nuclear region. In some such embodiments, processing includes subtracting a background fluorescence or pixel intensity from the nuclear fluorescence or pixel intensity. Further, in some embodiments, processing includes calculating an area of the nuclear region, for example, to multiply the area by the pixel intensity to calculate an integrated fluorescence density of the nuclear region. In some embodiments, processing includes comparing the first pixel intensity of a first nuclear region in a first cell to a second pixel intensity of a second nuclear region of a second cell, for example to normalize staining intensity across cells or to identify one or more outliers indicative of a rare cell, for example a circulating tumor cell. In some embodiments, the method includes processing the image to improve a signal-to-noise quality of the image. Non-limiting examples of processing include: adjusting a gain; adjusting an offset; averaging a plurality of scans of each pixel to determine an intensity of the pixel; or any other method.

As shown in FIG. 3, one embodiment of a computer-implemented method 300 of identifying a cell as a circulating tumor cell includes block S340, which recites analyzing the parameter of interest. In some embodiments, analyzing is performed using a machine-learning technique. In some such embodiments, the machine learning technique comprises: Classification Trees, Discriminant Analysis, k-Nearest Neighbors, Naive Bayes, Support Vector Machines, deep learning, or convolutional neural network. In one embodiment, the machine learning technique comprises deep learning. In another embodiment, the machine learning technique comprises convolutional neural network. In some embodiments, the result of the analysis is fed back into the system, for example using a feedback loop, so that the system improves its ability to identify features and/or to process said features to extract parameters of interest. In some embodiments, the analysis is supervised by a user, so that the user can, for example identify false positives or negatives to increase an accuracy of the analysis of the features and parameters of interest.

As shown in FIG. 3, one embodiment of a computer-implemented method 300 of identifying a cell as a circulating tumor cell includes block S350, which recites when the parameter of interest is greater than or less than a predetermined threshold, classifying the cell of interest as a circulating tumor cell. In some embodiments, the cell of interest is classified as the circulating tumor cell when the parameter of interest is greater than two, indicating an abnormally high DNA content. In some embodiments, the cell of interest is classified as the circulating tumor cell when the parameter of interest is less than one, indicating an abnormally low DNA content. In some embodiments, when the cell of interest is negative for a proliferation marker and the parameter of interest is between one and two, the cell of interest is classified as the circulating tumor cell. In some embodiments, the method includes excluding mitotic cells by excluding cells in the sample that are positive for proliferation and/or mitosis markers. In some embodiments, the method includes excluding apoptotic or necrotic cells, for example by excluding cells in the sample that are positive for apoptosis and/or necrosis makers.

In some embodiments, the method includes calculating a confidence score for the classification of the cell of interest or a probability that the cell of interest is a circulating tumor cell.

Devices

In some embodiments, the methods described herein can be embodied and/or implemented at least in part as a machine configured to receive a computer-readable medium storing computer-readable instructions. The instructions may be executed by computer-executable components integrated with the system and one or more portions of the processor on a computing device configured with an application comprising computer readable instructions for execution by a processor. The computer-readable medium can be stored on any suitable computer-readable media such as RAMs, ROMs, flash memory, EEPROMs, optical devices (e.g., CD or DVD), hard drives, floppy drives, or any suitable device. The computer-executable component may be a general or application-specific processor, digital signal processor, or other programmable logic device, but any suitable dedicated hardware or hardware/firmware combination can alternatively or additionally execute the instructions.

Figure 4:
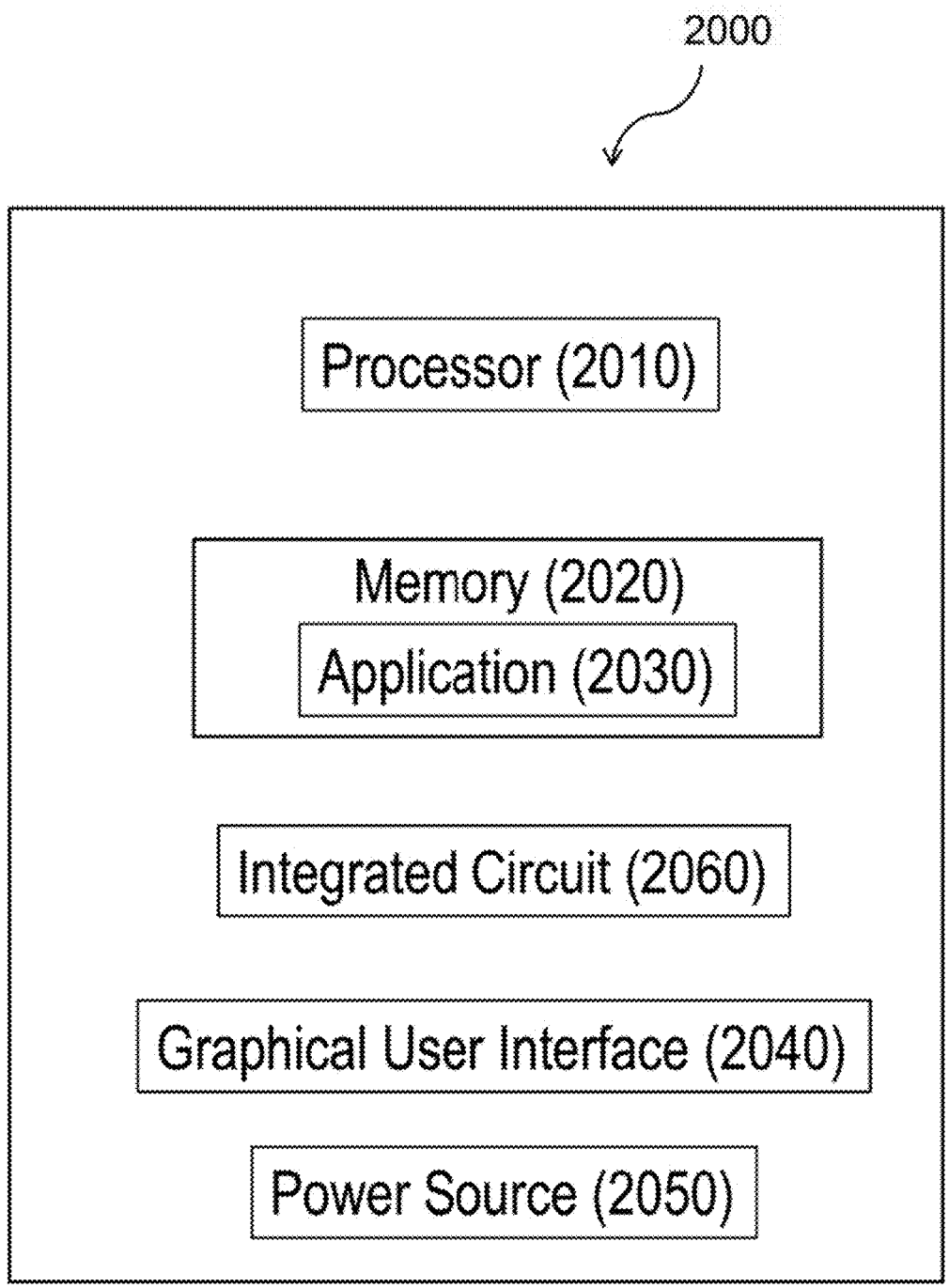
FIG. 4 is a schematic of a computing device configured to perform the methods of FIGS. 1-3.

In some embodiments, the methods described herein may be performed manually; in some embodiments, the methods described herein may be performed partially or wholly automatically, for example by a computing device 2000. A computing device 2000 may be a stationary or mobile computing device. Non-limiting examples of stationary computing devices include: a workstation, desktop, or any other non-portable computing device. Non-limiting examples of mobile computing devices include: a laptop, a netbook, a notebook, a mobile phone, a wearable device, or any other suitable mobile computing device. In some embodiments, as shown in FIG. 4, a computing device 2000 for identifying a cell as a circulating tumor cell includes a processor 2010, memory 2020, and optionally one or more applications 2030 stored in memory 2020. The processor 2010 is connected to the memory 2020 via one or more data buses. The processor 2010 functions to read information from and write information to memory 2020. The memory 2020 may be any type of computer-readable medium that stores computer-readable instructions for execution by the processor. Non-limiting examples of computer-readable medium include: RAM, ROM, flash memory, EEPROM, a hard disk drive, a solid state drive, or any other suitable device. In some embodiments, the computer-readable instructions include software stored in a non-transitory format. In some embodiments, the computer-readable instructions may be programmed into the memory 2020 or downloaded as an application 2030 onto the memory 2020. The processor 2010 may execute one or more sets of instructions to effect the functioning of the computer, for example to run an operating system, to run one or more applications, or to perform a method of identifying a cell as a circulating tumor cell. Some such methods are described in more detail elsewhere herein.

In some embodiments, as shown in FIG. 4, the computing device 2000 includes a graphical user interface (GUI) 2040. In some such embodiments, the GUI 2040 may display one or more cells or a population of cells that are analyzed by the processor 2010 to identify any one or more of the cells as a circulating tumor cell. Alternatively or additionally, the GUI 2040 may include one or more controls to alter one or more parameters, the functioning of the software, or a GUI appearance. In some embodiments, the GUI 2040 includes touch responsive capabilities such that it comprises, for example, a Thin Film Transistor liquid crystal display (LCD), an in-place switching LCD, a resistive touchscreen LCD, a capacitive touchscreen LCD, an organic light emitting diode (LED), an Active-Matrix organic LED (AMOLED), a Super AMOLED, a Retina display, a Haptic/Tactile touchscreen, Gorilla Glass, or Quantum Dot Display.

In some embodiments, as shown in FIG. 4, the computing device 2000 includes a power source 2050. The power source 2050 may power the computing device 2000 via alternating current from an outlet. Alternatively, the power source 2050 may include a battery, for example a rechargeable battery (e.g., lithium ion).

In some embodiments, the computing device 2000 includes an integrated circuit 2060. In some such embodiments, the integrated circuit may include an operational amplifier, a low-pass, high-pass, or band-pass filter, an analog-to-digital (AD) converter, and/or other signal processing circuit components configured to filter, amplify, digitize, or otherwise process an image of a cell to extract one or more pixel intensities or one or more parameters of interest, as described elsewhere herein.

FIXING AND STAINING—EXAMPLES

The following are examples of use of the methods described elsewhere herein for fixing and staining cells and identifying a circulating tumor cell in a cell sample. The samples were prepared according to the methods and compositions described elsewhere herein. Although specific examples are used, it will be appreciated by one of skill in the art that the methods described herein may be used in examples beyond what is presented herein.

Experiment setup. Peripheral venous blood was drawn from healthy volunteers. Red blood cells were lysed using ammonium chloride lysing buffer. White blood cells were washed twice in PBS. The cancer cell line A549 was grown in RPMI with 10% FBS at 5% CO2 in T75 cell culture flasks. Cells were harvested with trypsin/EDTA.

For each experiment unless otherwise indicated, 20,000 cancer cells were spiked into 200,000 white blood cells. Cells were then resuspended in variations of cytocentrifugation buffer as indicated. Gelatin-coated glass slides were mounted into Cytofuge II chambers and spun for ten minutes at 600 rpm in a Medite CytofugeII (Germany). Chambers were then removed from the Cytofuge, and slides unmounted. Care was taken not to let slides with deposited cells dry up entirely. Slides were then incubated in variations of the extracellular fixing buffer as indicated. After thirty minutes, slides were removed, excess liquid briefly blotted onto filter paper while holding slides upright, and immersed in variations of the intracellular fixing buffer as indicated. After another sixty minutes, slides were removed from the intracellular fixing buffer, mounted onto Coverplates (Thermofisher) and blocked and stained as indicated.

Fixing and Staining—Example 1

Figure 5A:
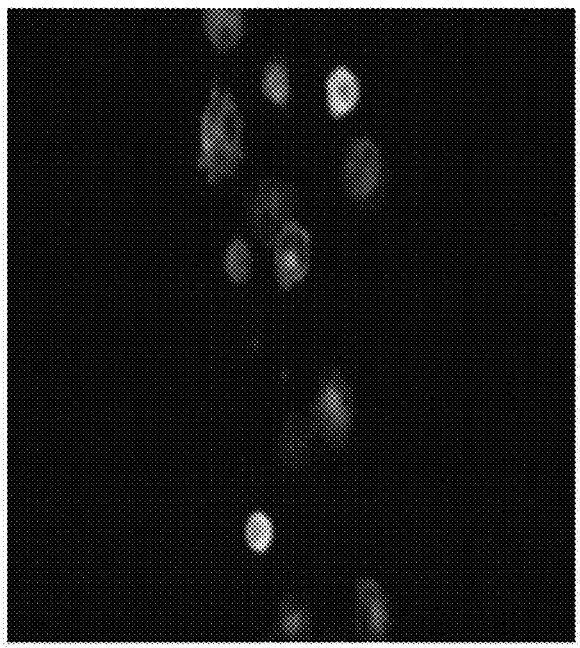
Figure 5B:
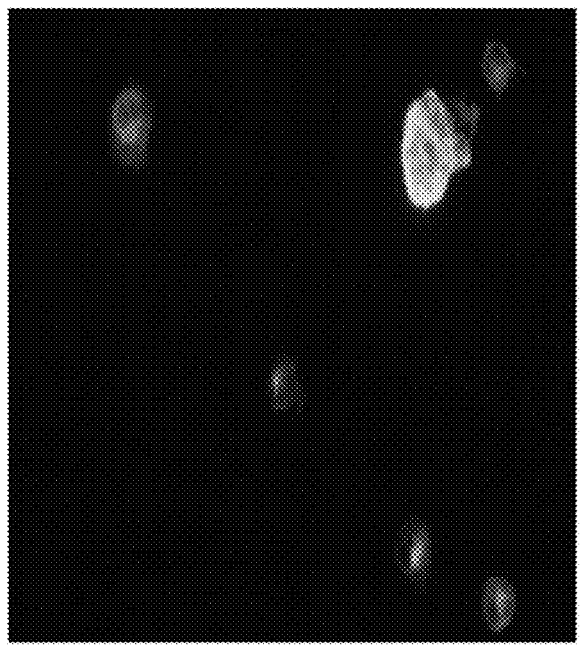
FIG. 5B shows one example of an experimental result in which cells were cytocentrifuged in a buffer including 1% w/v PVP and 0.01% w/v Chromium Potassium Sulfate diluted in PBS.
Figure 5C:
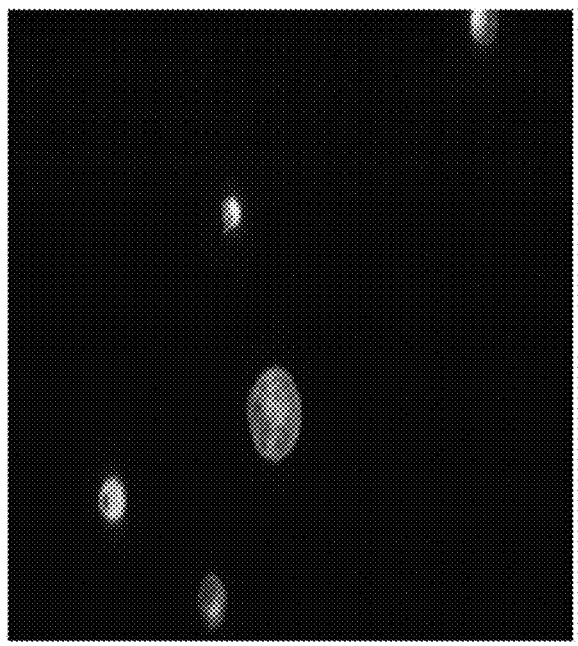
FIG. 5C shows one example of an experimental result in which cells were cytocentrifuged in a buffer including 10% w/v PVP and 0.01% w/v Chromium Potassium Sulfate diluted in PBS.
Figure 5D:
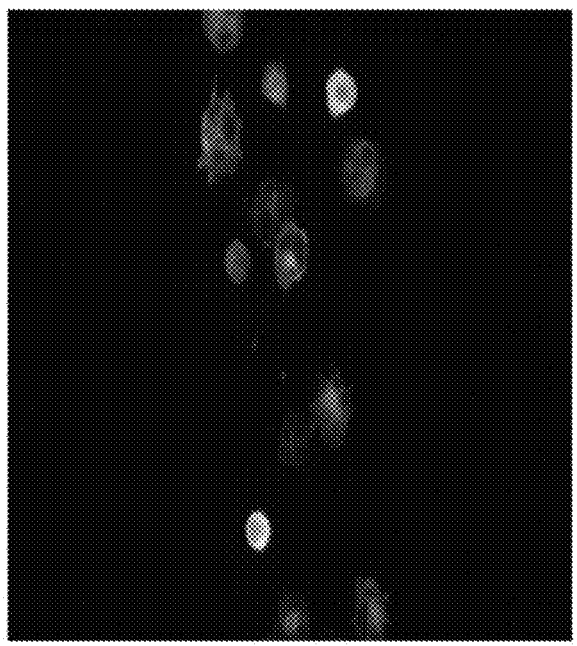
FIG. 5D shows one example of an experimental result in which cells were cytocentrifuged in a buffer including 20% w/v PVP and 0.01% w/v Chromium Potassium Sulfate diluted in PBS.

Cytocentrifugation Buffer. The amount of hydrophilic polymer (e.g., PVP) in the cytocentrifugation buffer was varied while the fixing and staining methods remained constant. As shown in FIGS. 5A, 5B, and 5D, the cytocentrifugation buffer includes 0%, 1%, or 20% PVP, respectively. All conditions included a fixed amount of fixative in the cytocentrifugation buffer: 0.01% w/v chromium potassium sulfate. As shown in FIGS. 5A, 5B, and 5D, the cells appear irregular with disrupted extracellular membranes, extracellular membrane blebbing (i.e., bulge, or protrusion of the plasma membrane of a cell), and staining artifacts appearing intracellularly. In contrast, as shown in FIG. 5C, when the cytocentrifugation buffer includes 10% PVP, the cells appear spherical and intact with minimal extracellular membrane disruption or blebbing.

Fixing and Staining—Example 2

Figure 6A:
FIG. 6A shows one example of an experimental result in which cells were fixed at −10° C. with an extracellular fixative comprising 100% methanol.
Figure 6B:
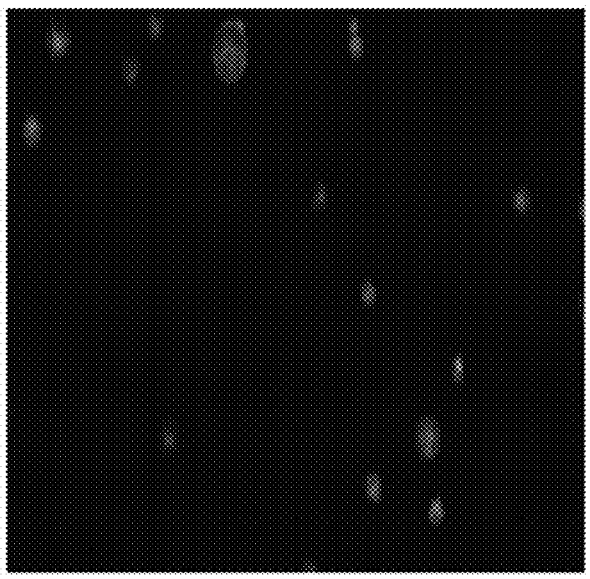
FIG. 6B shows one example of an experimental result in which cells were fixed on dry ice with an extracellular fixative comprising 100% methanol.
Figure 6C:
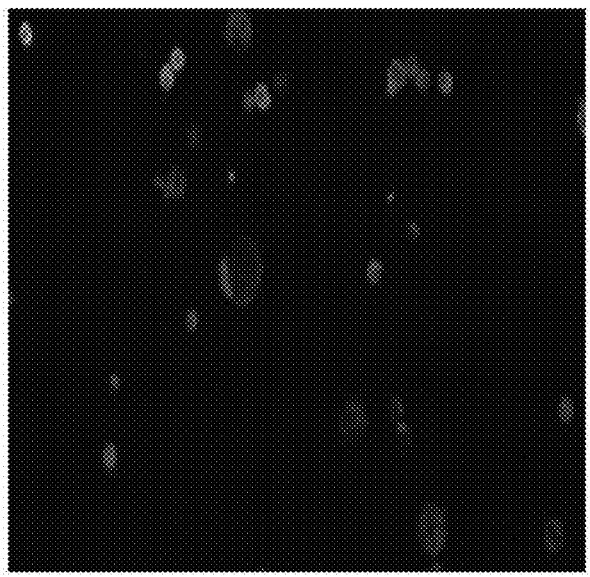
FIG. 6C shows one example of an experimental result in which cells were fixed at −10° C. with an extracellular fixative comprising 1% w/v PVP diluted in methanol.
Figure 6D:
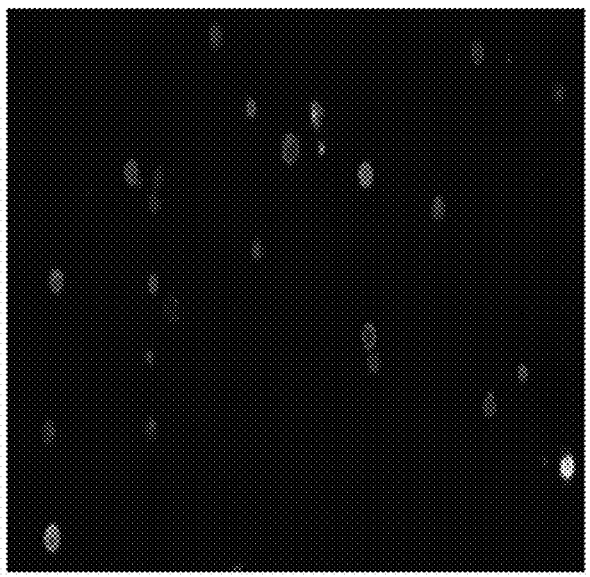
FIG. 6D shows one example of an experimental result in which cells were fixed on dry ice with an extracellular fixative comprising 1% w/v PVP diluted in methanol.
Figure 6E:
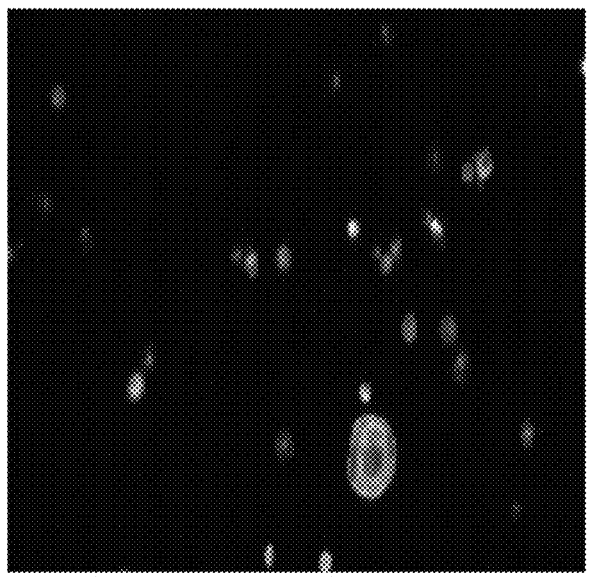
FIG. 6E shows one example of an experimental result in which cells were fixed at −10° C. with an extracellular fixative comprising 5% w/v PVP diluted in methanol.
Figure 6F:
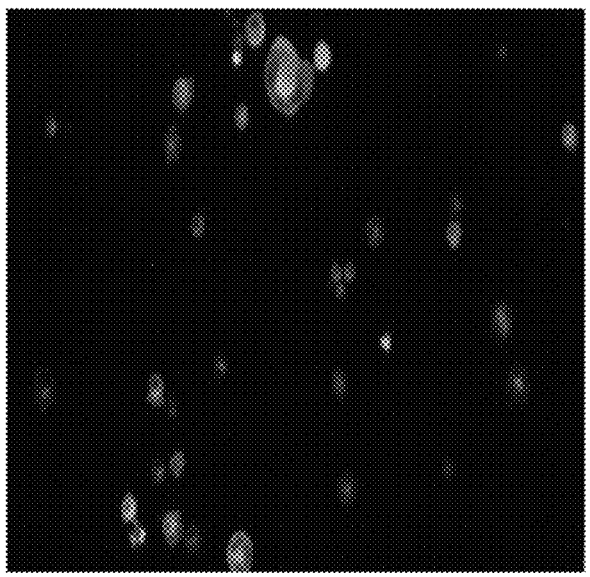
FIG. 6F shows one example of an experimental result in which cells were fixed on dry ice with an extracellular fixative comprising 5% w/v PVP diluted in methanol.
Figure 6G:
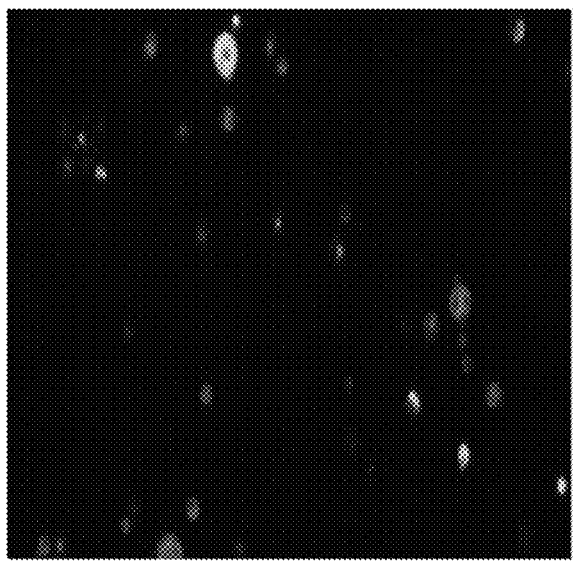
FIG. 6G shows one example of an experimental result in which cells were fixed at −10° C. with an extracellular fixative comprising 10% w/v PVP diluted in methanol.
Figure 6H:
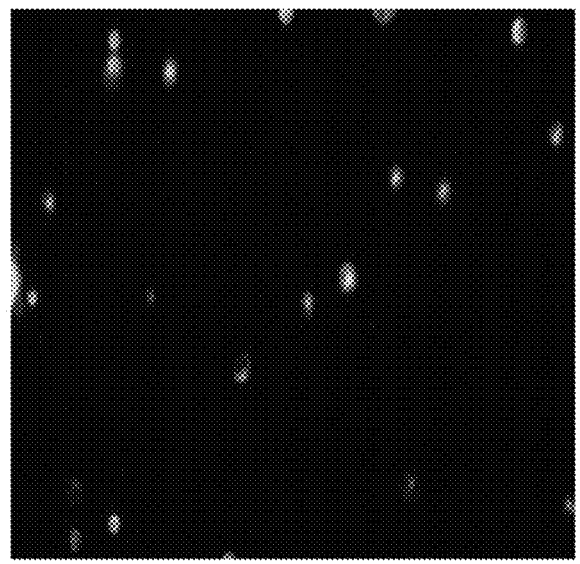
FIG. 6H shows one example of an experimental result in which cells were fixed on dry ice with an extracellular fixative comprising 10% w/v PVP diluted in methanol.

Extracellular Fixative. The amount of hydrophilic polymer in the extracellular fixative and the temperature at which the cells were fixed with the extracellular fixative were varied while the intracellular fixative, cytocentrifugation buffer, and staining methods remained constant. As shown in FIGS. 6A, 6C, 6E, and 6G, a temperature of −10° C. was used during fixation of the cells with the extracellular fixative. As shown in FIGS. 6B, 6D, 6F, and 6H, the cells were fixed with the extracellular fixative while on dry ice (e.g., substantially or about −60° C. to −110° C.). As shown in FIG. 6F, cells fixed on dry ice in 5% w/v hydrophilic polymer (e.g., PVP) diluted in methanol have improved integrity, reduced artifacts, and enhanced staining, as compared to cells fixed with an extracellular fixative comprising less (FIGS. 6A-6D) or more (FIG. 6G-6H) hydrophilic polymer or cells fixed at −10° C. (FIGS. 6A, 6C, 6E, and 6G) instead of on dry ice (FIGS. 6B, 6D, 6F, and 6H).

Fixing and Staining—Example 3

Figure 7A:
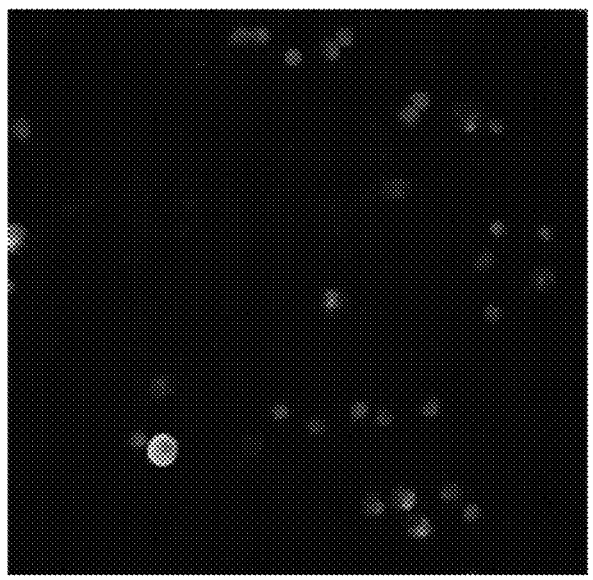
FIGS. 7A-7F show experimental results in which A549 cells were stained with anti-cytokeratin (shown in green) and anti-CD45 (shown in yellow).
Figure 7B:
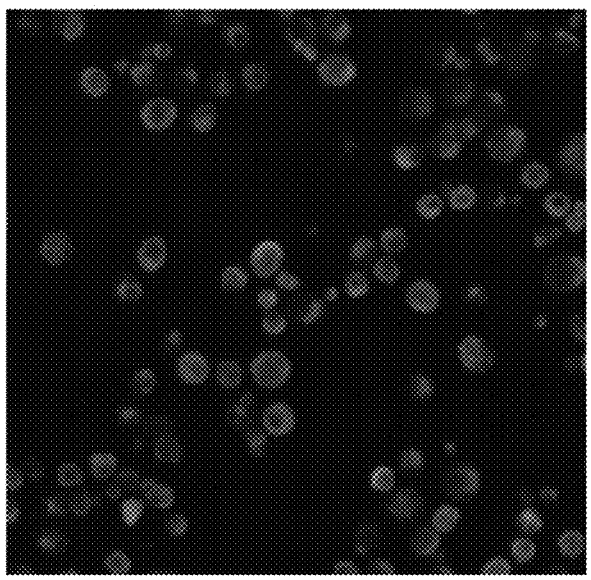
Figure 7C:
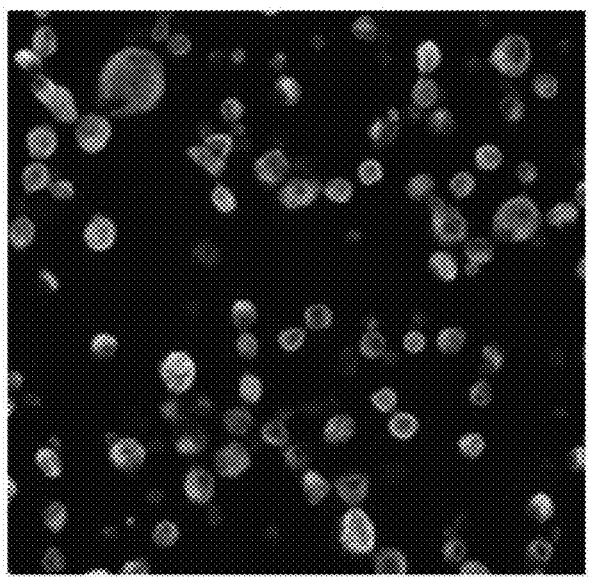
Figure 7D:
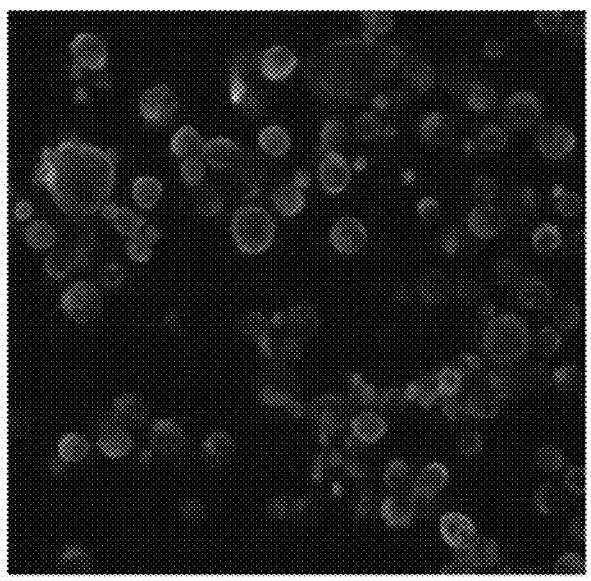
Figure 7E:
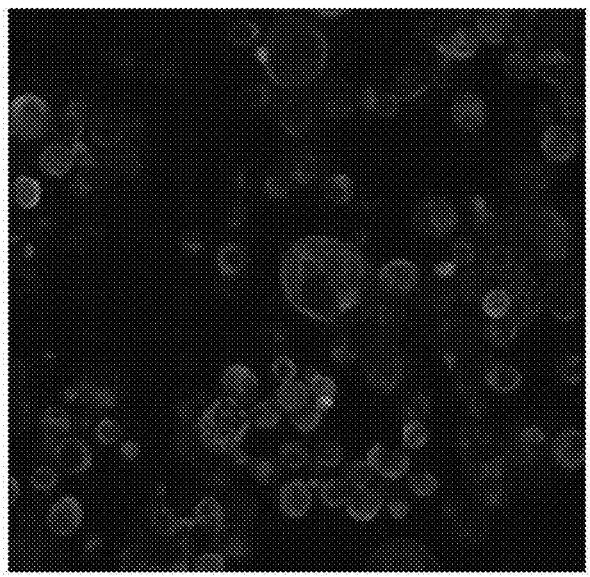
Figure 7F:
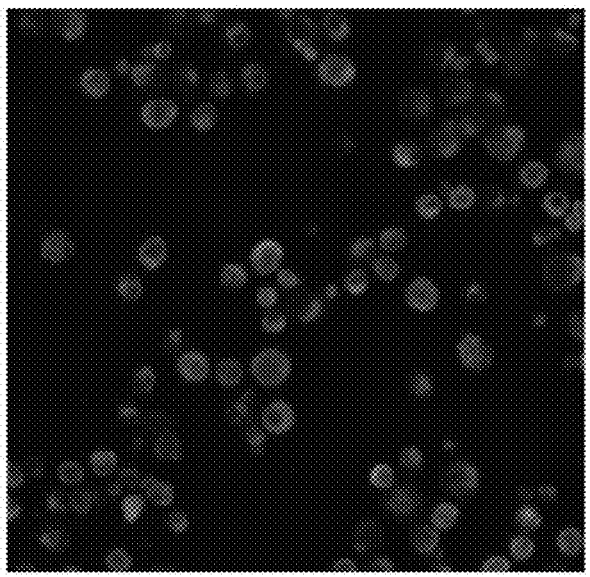

Intracellular Fixative. The amount of hydrophilic polymer (e.g., glycerol) in the intracellular fixative and the temperature at which the cells were fixed with the intracellular fixative were varied while the extracellular fixative, cytocentrifugation buffer, and staining methods remained constant. As shown in FIGS. 7A-7D, there was a fixed amount of detergent and chromium potassium sulfate in the intracellular fixative: 0.4% v/v Tween20 and 0.01% w/v chromium potassium sulfate. As shown in FIG. 7A, when cells are fixed at room temperature, most of the cells are lost and the few remaining cells have reduced integrity, increased degradation, and increased artifacts. As shown in FIG. 7B, when the cells are fixed at substantially or about −2° C., the cells have an intact extracellular membrane, reduced artifacts, and improved staining. As shown in FIGS. 7A and 7B, a freezing (e.g., about 0° C.) or slightly sub-freezing temperature (e.g., −1° C. to −4° C.) is advantageous during fixation with the intracellular fixative to prevent cell loss (e.g., to apoptosis, cell death, etc.) and to improve and/or maintain cell integrity. As shown in FIGS. 7C and 7D, higher concentrations of glycerol improve cellular morphology. As shown in FIGS. 7E and 7F, the amount of fixative (e.g., chromium potassium sulfate) was varied and the amount of hydrophilic polymer and detergent were fixed: 15% v/v glycerol and 0.4% v/v Tween20. As shown in FIG. 7E, omitting chromium potassium results in cell loss and worse preservation of cellular morphology. As shown in FIG. 7F, 15% v/v glycerol with 0.01% w/v chromium potassium sulfate results in optimal resolution of cellular detail and substantially no cell loss.

Fixing and Staining—Example 4

Figure 8A:
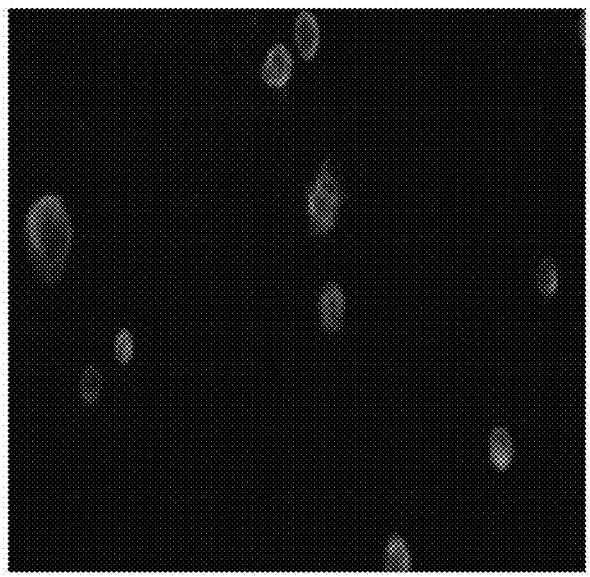
FIG. 8A shows one example of an experimental result in which cells were blocked with a blocking buffer prior to staining. The blocking buffer included 2% w/v bovine serum albumin (BSA).
Figure 8B:
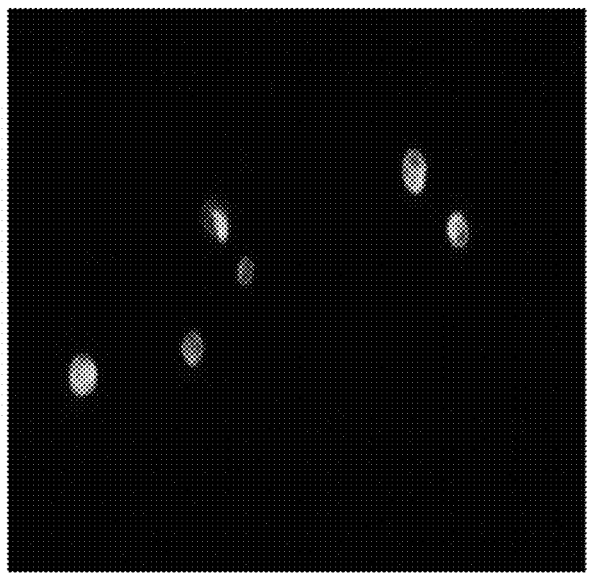

Blocking Buffer. The type of irrelevant protein was altered between FIGS. 8A and 8B, while the amount of irrelevant protein, hydrophilic polymer, detergent, and amino acid remained constant: 2% w/v irrelevant protein, 15% v/v hydrophilic polymer (e.g., glycerol), 0.4% v/v detergent (e.g., Tween20), and 0.3M glycine. As shown in FIG. 8A, when bovine serum albumin is used in the blocking buffer, the stain is dull and the specific staining has the intensity of background staining making identification of the specifically stained features difficult. As shown in FIG. 8B, when hydrolyzed collagen is used, the stain is bright and specific areas of high staining are easily identifiable as compared to background staining.

Fixing and Staining—Example 5

Figure 9A:
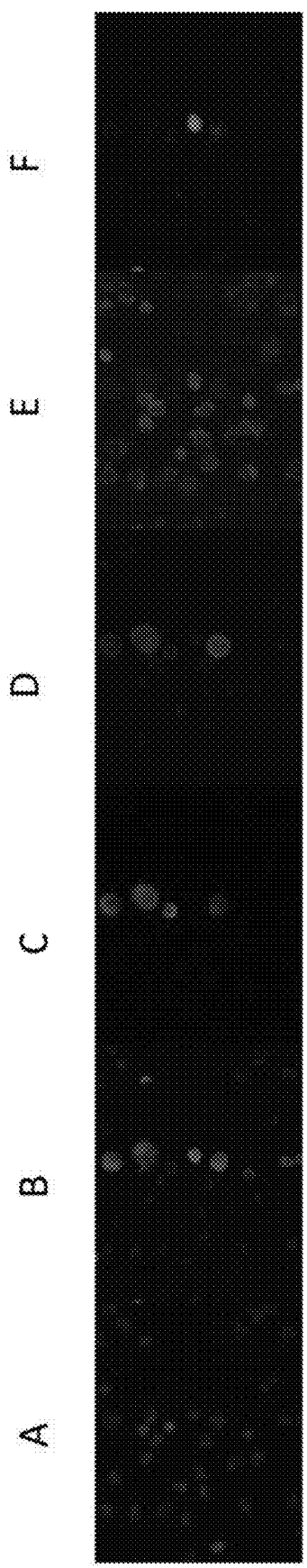
FIG. 9A shows white blood cells spiked with A549 cells fixed with 10% w/v PVP and 0.01% w/v chromium potassium sulfate according to the methods described in FIG. 1 and stained with DRAQ5 (Panel A), AlexaFluor488-Vimentin (Panel B), AlexaFluor594-pan-Cytokeratin (Panel C), PE-EpCam (Panel D), Pacific Orange-CD45 (Panel E), and BV421-CD14 (Panel F).

Immunofluorescence staining. As shown in FIG. 9A, cells were cytocentrifuged onto standard laboratory slides and processed by the methods described in FIG. 1 and elsewhere herein. The cells were stained with DRAQ5 (nucleus) as shown in Panel A in FIG. 9A, AlexaFluor488-Vimentin as shown in Panel B in FIG. 9A, AlexaFluor594-pan-Cytokeratin as shown in Panel C in FIG. 9A, PE-EpCam as shown in Panel D in FIG. 9A, Pacific Orange-CD45 as shown in Panel E in FIG. 9A, and BV421-CD14 as shown in Panel F in FIG. 9A. As shown in FIG. 9A, nuclear and cellular structures are preserved. Vimentin (FIG. 9A, Panel B), cytokeratin (FIG. 9A, Panel C), and EpCam (FIG. 9A, Panel D) exhibit markedly different cellular distribution and structure. Further, WBC and CD14 (FIG. 9A, Panel F) positive cells can be easily distinguished from cancer cells.

Figure 9B:
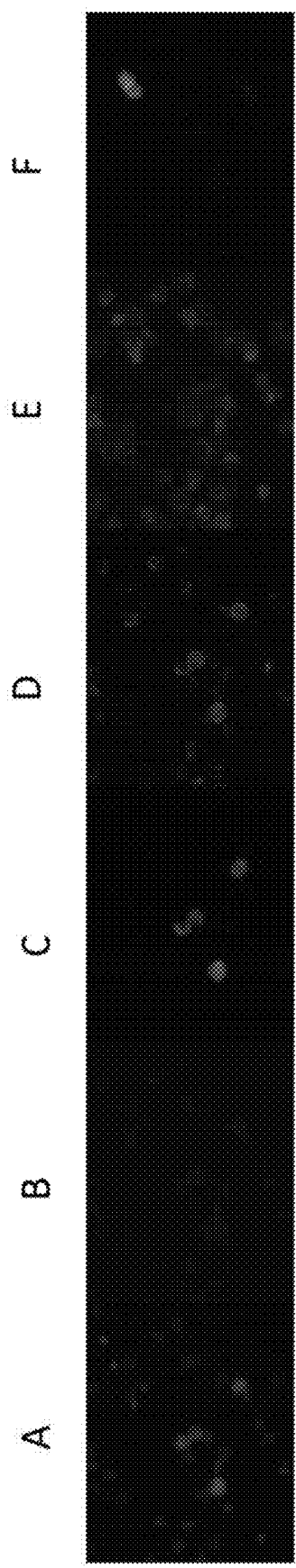
FIG. 9B shows white blood cells spiked with A549 cells fixed with 4% paraformaldehyde and stained with DRAQ5 (Panel A), AlexaFluor488-Vimentin (Panel B), AlexaFluor594-pan-Cytokeratin (Panel C), PE-EpCam (Panel D), Pacific Orange-CD45 (Panel E), and BV421-CD14 (Panel F).

As shown in FIG. 9B, cells from the same donor and the same cell culture batch as FIG. 9A, on the same day, were fixed with paraformaldehyde 4%, perforated with 0.5% saponin, blocked and stained with DRAQ5 (nucleus) as shown in Panel A in FIG. 9B, AlexaFluor488-Vimentin as shown in Panel B in FIG. 9B, AlexaFluor594-pan-Cytokeratin as shown in Panel C in FIG. 9B, PE-EpCam as shown in Panel D in FIG. 9B, Pacific Orange-CD45 as shown in Panel E in FIG. 9B, and BV421-CD14 as shown in Panel F in FIG. 9B. As shown in FIG. 9B, the nuclei (FIG. 9B, Panel A) of the WBC appear diffuse, the morphology and distribution of Cytokeratin (FIG. 9B, Panel C) and EpCam (FIG. 9B, Panel D) appears highly similar, and the morphology of WBC and CD14 (FIG. 9B, Panel F) positive cells is distorted. Further, as shown in Panel B in FIG. 9B, vimentin does not stain. Also, high autofluorescence of WBC is observed in the PE channel as shown in Panel D in FIG. 9B.

Fixing and Staining—Example 6

RNA Recovery. 500,000 cells from the lung cancer cell line, A549, were spun onto slides using a Cytofuge 2 (Statspin, USA) and RNA recovery was compared after fixing with 10% w/w PVP and 0.01% w/v chromium potassium sulfate and staining according to the methods described in FIG. 1 versus the two most frequently used methods, paraformaldehyde (PFA) and methanol fixation.

For PFA fixation, slides were dried for five minutes at room temperature, immersed in 4% PFA for ten minutes, washed with PBS, incubated in PBS/Saponin 0.5% for ten minutes, and washed in PBS again. Then, slides were blocked in PBS/BSA 1%/Tween 20 0.1%/Glycine 0.3M for thirty minutes, mock-stained in PBS/BSA 1% for sixty minutes, and washed with PBS before being mounted with coverslips.

For methanol fixation, slides were dried for five minutes at room temperature and immersed in −20° C. chilled 100% methanol for ten minutes. Slides were then blocked in PBS/BSA 1%/Tween 20 0.1%/Glycine 0.3M for thirty minutes, mock-stained in PBS/BSA 1% for sixty minutes, and washed with PBS before being mounted with coverslips.

All slides were maintained at 4° C. for forty-eight hours until removal of coverslips for analysis of RNA content.

For RNA extraction, commercial RNA extraction kits were used (Jena bioscience, Germany). The coverslip was removed and hydrophobic ink circles were drawn around the cells on the slides. Five hundred microliters of lysis buffer was applied and incubated for five minutes at room temperature. Samples were aspirated and mixed with 300 microliters isopropanol. Mini-spin columns were prepared with activation buffer according to the instructions of the manufacturer and samples added to the column. After centrifugation at 10,000 g for thirty seconds, the flow through was discarded and columns were washed two times with washing buffers supplied by the manufacturer. Then, the spin column was placed into a new microcentrifuge tube. Forty microliters of elution buffer was added to each column and incubated for one minute at room temperature. Then columns were centrifuged at 10,000 g for one minute and RNA obtained in the flow through was measured in a Qbit Fluorometer 3.0 (Thermo Fisher). RNA quantity was compared to total RNA obtained from fresh cells obtained from the same culture on the same day as the fixation of the other samples and then stored at 4° C. in RPMI 1640 media with 10% FBS during the forty-eight hours. Fresh cells were washed in PBS and re-counted before RNA extraction.

Figure 10:
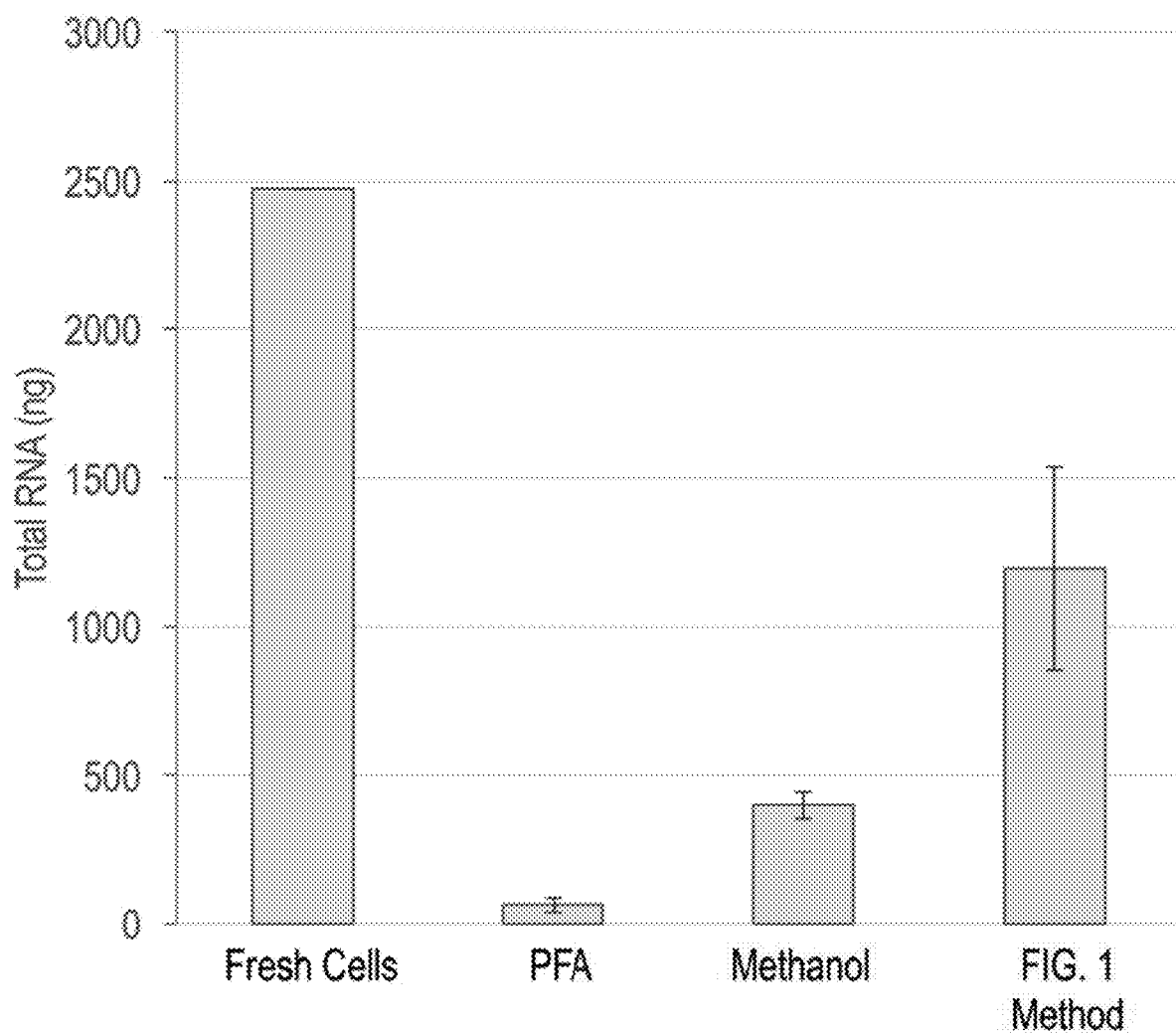
FIG. 10 shows a histogram depicting total RNA content in nanograms of 500,000 fresh cells or cells fixed using paraformaldehyde, methanol, or according to the method described in FIG. 1.

As shown in FIG. 10, the methods described in FIG. 1 and elsewhere herein preserve up to 70% of RNA as compared to fresh cells, while methanol and PFA fixation results in substantial loss of RNA. Therefore, the methods and compositions described herein offer a unique advantage to facilitate downstream molecular biology methods, for example, genetic analysis, transcriptome analysis, and next-generation RNA sequencing.

IDENTIFYING CTC—EXAMPLES

The following are examples of use of the methods described elsewhere herein for identifying a circulating tumor cell in a cell sample. The samples were prepared according to the methods and compositions described elsewhere herein. Although specific examples are used, it will be appreciated by one of skill in the art that the methods described herein may be used in examples beyond what is presented herein.

Integrated fluorescence density or pixel intensity of a nuclear area of a cell of interest is a valuable marker for identifying circulating cancer cells. DNA content of cells can serve as an important indicator to confirm or exclude malignancy if combined with immunostaining of membrane (CD45, CD34, CD14, white blood cell markers), cytosolic (vimentin), and/or nuclear antigens (e.g., H3 Ser10, a mitosis marker; caspase-3, an apoptosis marker).

As shown and described elsewhere herein, a two-fold increase in nuclear DNA content can be found in healthy white blood cells (WBC) undergoing mitosis. However, WBC undergoing mitosis is a very rare occurrence in healthy individuals (for example, less than one cell per 500,000 WBC). Healthy, mitotic WBC are characterized by expression of WBC markers CD45 and/or CD14 and/or others, as well as by phosphorylation at Serine 10, Histone 3, which is widely reported in the literature and sometimes used in routine diagnostics for detection of mitotic cells.

However, any two-fold increase of nuclear DNA content not accompanied by phosphorylation of Serine 10, Histone 3 (no binding of anti-H3Ser10 antibody), or any increase other than two-fold, especially any increase larger than two-fold, is a strong indicator for malignancy of cells found in the circulation. Any decrease in nuclear DNA content must be evaluated together with hematopoietic stem cell markers, such as CD34, with apoptosis markers such as caspase-3, and in clinical context, for example, excluding the presence of Thalassemia or other diseases leading to elevated frequencies of apoptotic cells in the circulation. Note that prolonged storage of whole blood can also lead to increase frequencies of apoptotic cells.

Identifying CTC—Example 1

Figure 11A:
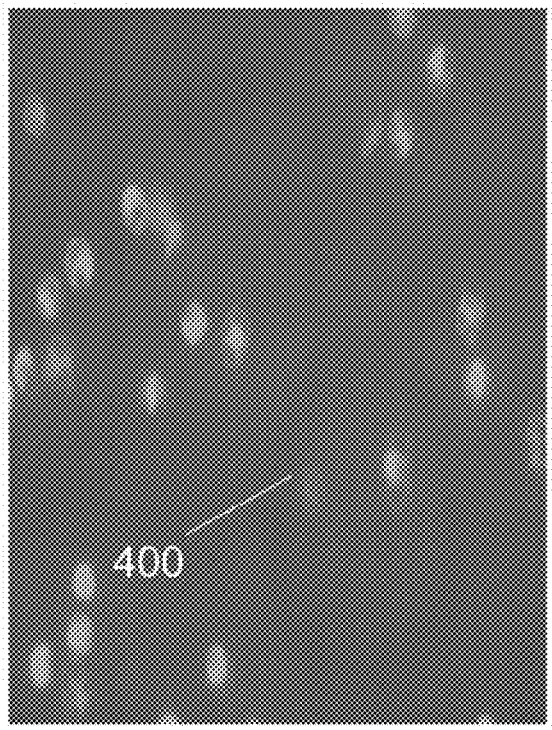
FIG. 11A shows a microscopy image of a BV421-CD45 stain of a prostate cancer cell sample.
Figure 11B:
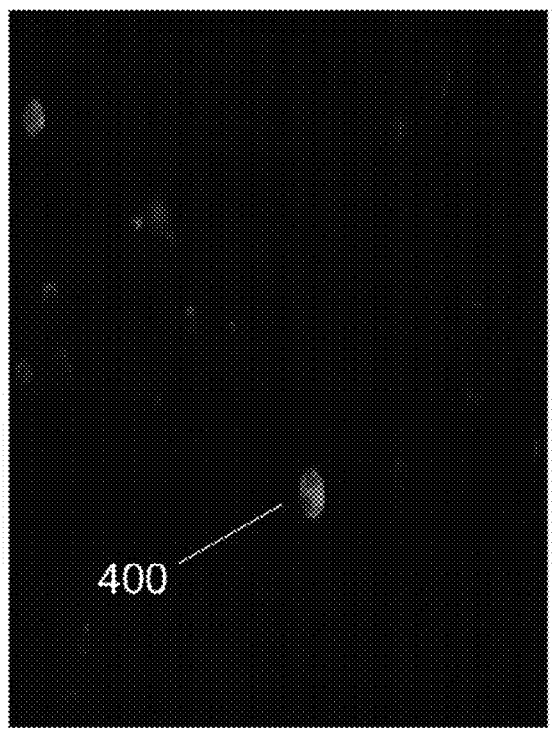
FIG. 11B shows a microscopy image of a DyLight594-Vimentin stain of a prostate cancer cell sample.
Figure 11C:
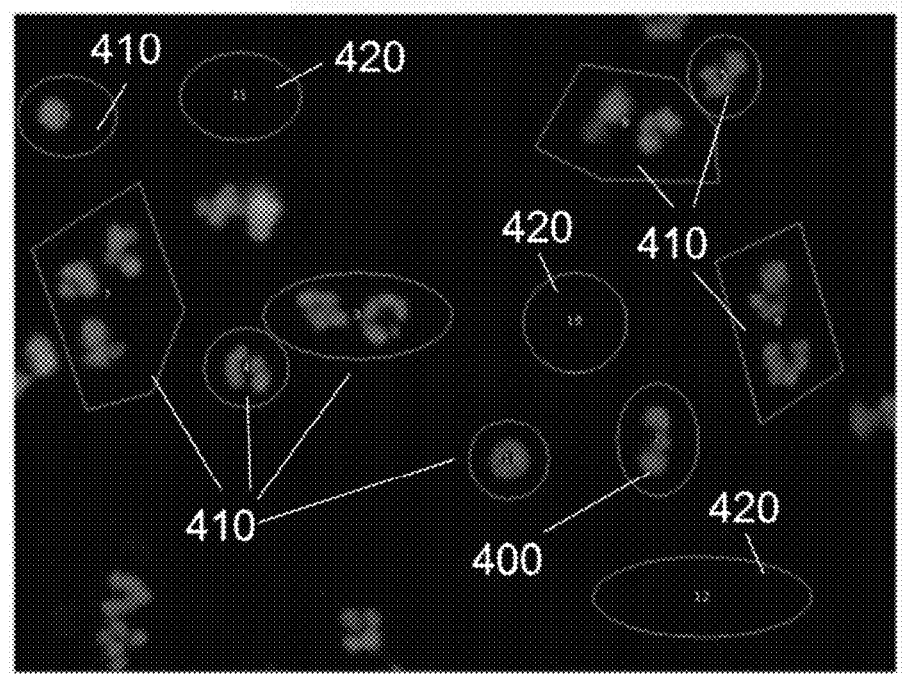
FIG. 11C shows a microscopy image of identification of a background area and a nuclear area of cells in a prostate cancer cell sample. The nuclear area is stained with DRAQ5.
Figure 11D:
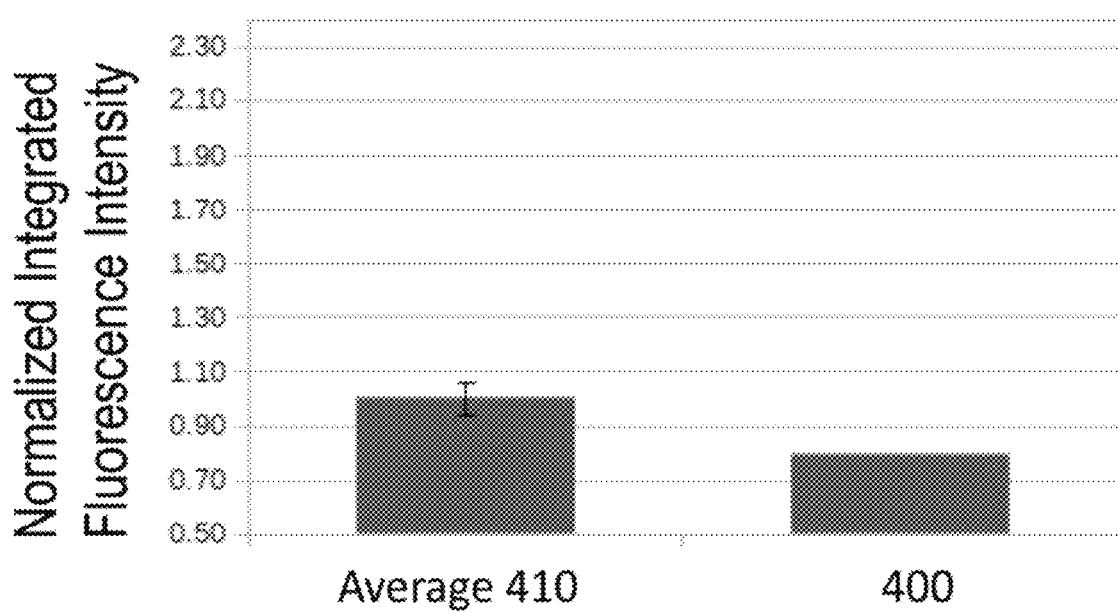
FIG. 11D shows a histogram depicting a ploidy status of a cell of interest.

FIG. 11A shows a microscopy image of a BV421-CD45 stain of a prostate cancer cell sample and FIG. 11B shows a microscopy image of a DyLight594-Vimentin stain of the same prostate cancer cell sample. In comparing FIGS. 11A-11B, there is a cell of interest 400 that is staining positive for Vimentin (FIG. 11B) but negative for CD45 (FIG. 11A). Nuclear staining of the cell of interest 400 with DRAQ5 as shown in FIG. 11C reveals that the cell of interest 400 has a reduced DNA content (0.79×), as shown in the histogram in FIG. 11D, as compared to other cells 410 in the cell sample when the cell of interest 400 and the other cells 410 are normalized to the background 420, as described in FIGS. 2-3 and elsewhere herein. These data are consistent with the cell of interest either being a circulating tumor cell or apoptotic. Further analysis with one or more apoptosis markers would be required to distinguish between these two possibilities.

Identifying CTC—Example 2

Figure 12A:
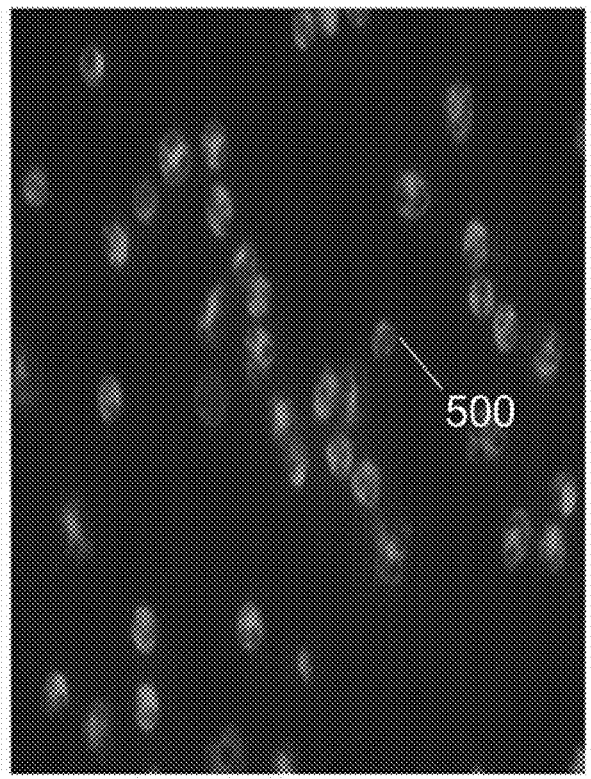
FIG. 12A shows a microscopy image of a BV421-CD45 stain of a prostate cancer cell sample.
Figure 12B:
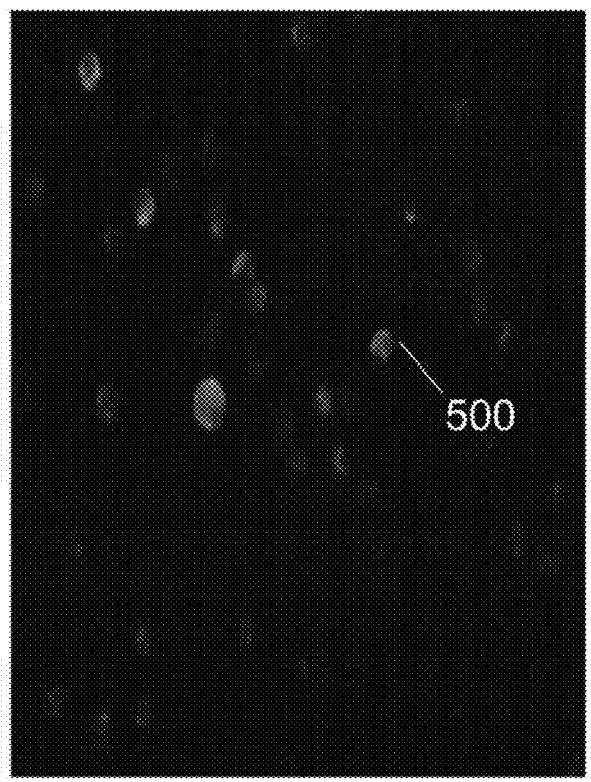
FIG. 12B shows a microscopy image of a DyLight594-Vimentin stain of a prostate cancer cell sample.
Figure 12C:
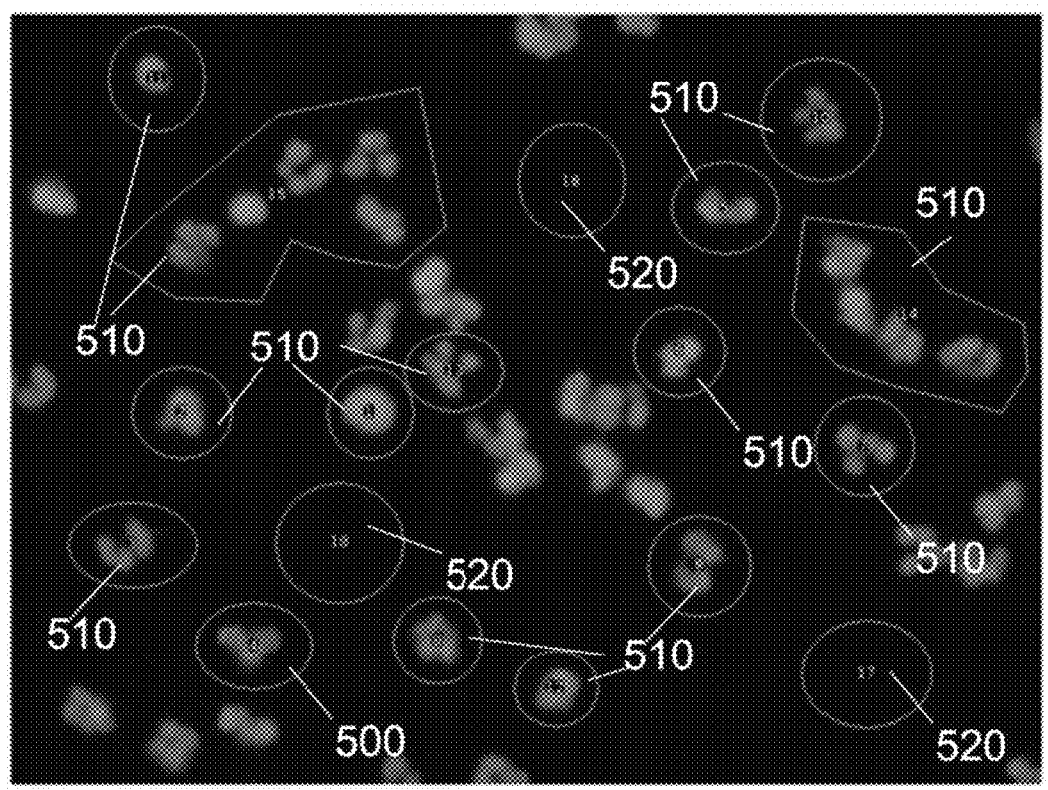
FIG. 12C shows an analysis of a microscopy image including identification of a background area and a nuclear area of cells in a prostate cancer cell sample. The nuclear area is stained with stained with DRAQ5.
Figure 12D:
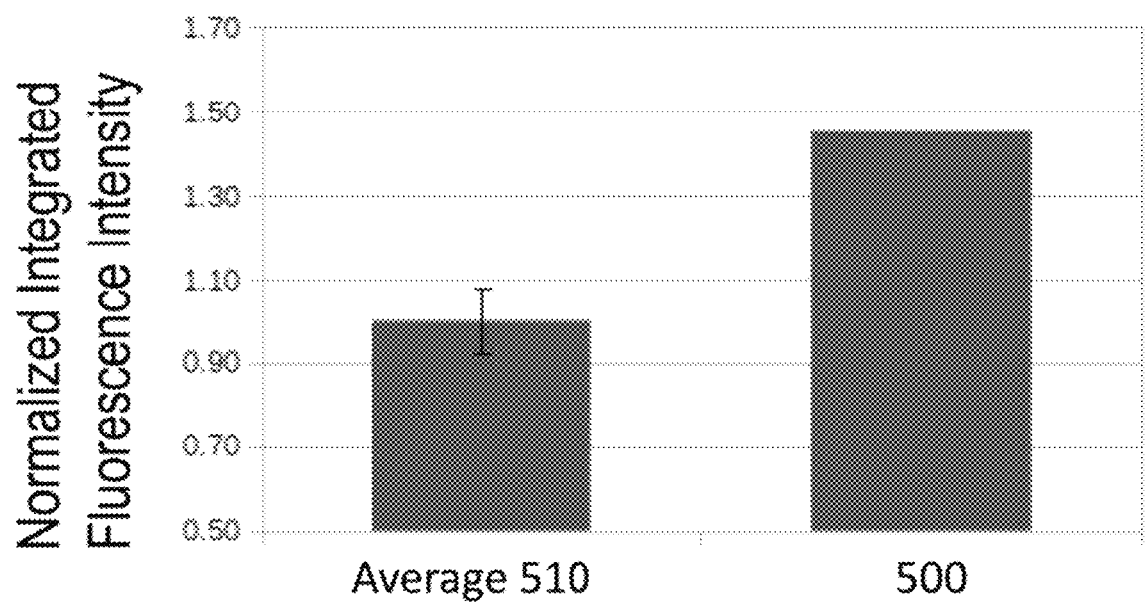
FIG. 12D shows a histogram depicting a ploidy status of a cell of interest.

FIG. 12A shows a microscopy image of a BV421-CD45 stain of a prostate cancer cell sample and FIG. 12B shows a microscopy image of a DyLight594-Vimentin stain of the same prostate cancer cell sample. In comparing FIGS. 12A-12B, there is a cell of interest 500 that is staining positive for Vimentin (FIG. 12B) but negative for CD45 (FIG. 12A). Nuclear staining of the cell of interest 500 with DRAQ5 as shown in FIG. 12C reveals that the cell of interest 500 has an increased DNA content (1.45×), as shown in the histogram in FIG. 12D, as compared to other cells 510 in the cell sample when the cell of interest 500 and the other cells 510 are normalized to the background 520, as described in FIGS. 2-3 and elsewhere herein. These data are consistent with the cell of interest either being aneuploidic or a circulating tumor cell. To confirm that the cell is not undergoing healthy mitosis, staining with a proliferation marker or mitosis marker would be required.

Identifying CTC—Example 3

Figure 13D:
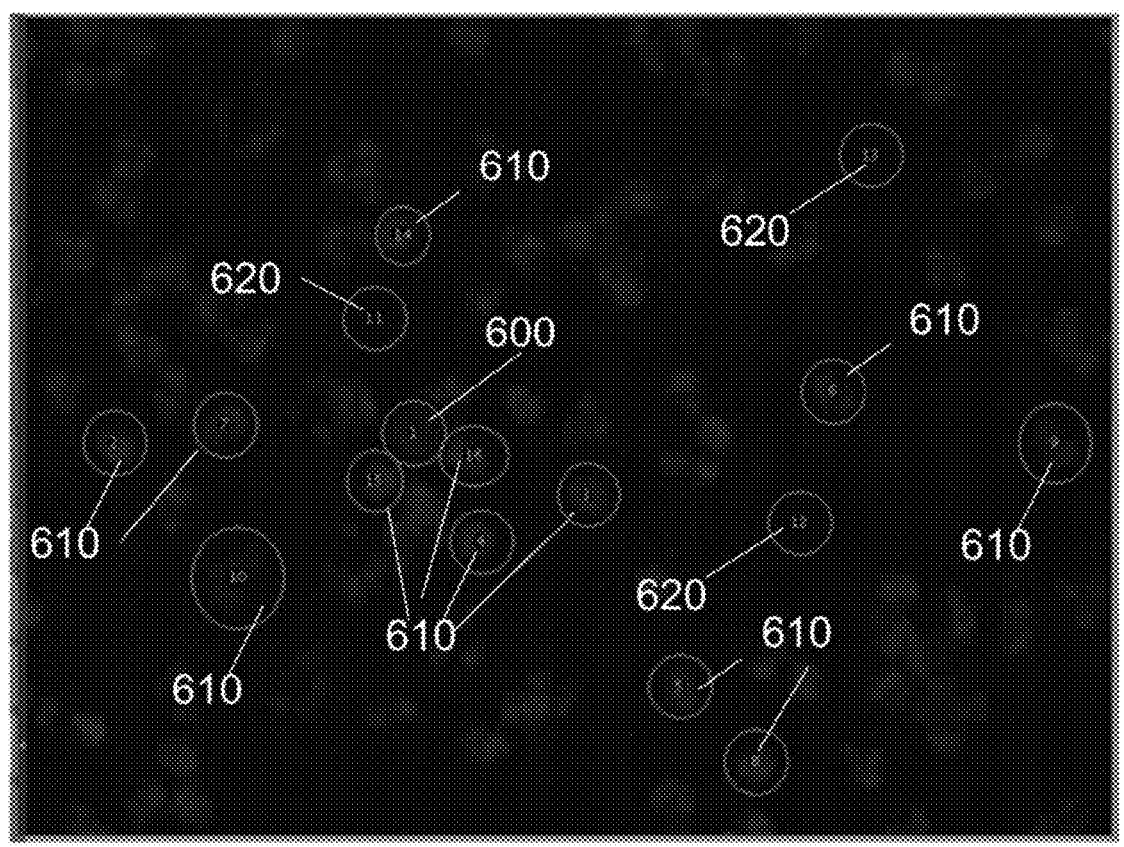
FIG. 13D shows an analysis of a microscopy image including identification of a background area and a nuclear area of cells in a prostate cancer cell sample. The nuclear area is stained with DRAQ5.
Figure 13E:
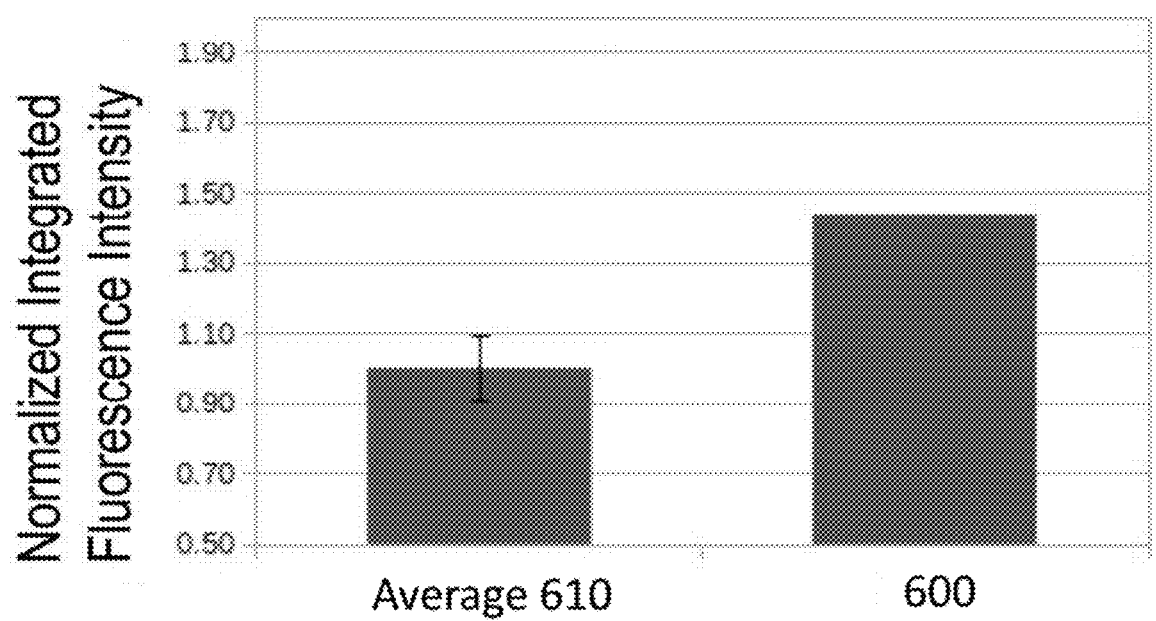
FIG. 13E shows a histogram depicting a ploidy status of a cell of interest.

FIG. 13A shows a microscopy image of a BV421-CD14 stain of a prostate cancer cell sample; FIG. 13B shows a microscopy image of a Pacific Orange-CD45 stain of the same prostate cancer cell sample; and FIG. 13C shows a microscopy image of a AlexaFluor488-Vimentin stain of the same prostate cancer cell sample. In comparing FIGS. 13A-13C, there is a cell of interest 600 that is staining positive for Vimentin (FIG. 13C) but negative for CD45 (FIG. 13B) and CD14 (FIG. 13A). Nuclear staining of the cell of interest 600 with DRAQ5 as shown in FIG. 13D reveals that the cell of interest 600 has an increased DNA content (1.44×), as shown in the histogram in FIG. 13E, as compared to other cells 610 in the cell sample when the cell of interest 600 and the other cells 610 are normalized to the background 620, as described in FIGS. 2-3 and elsewhere herein. These data are consistent with the cell of interest either being aneuploidic or a circulating tumor cell. To confirm that the cell is not undergoing healthy mitosis, staining with a proliferation marker or mitosis marker would be required.

Identifying CTC—Example 4

Figure 14A:
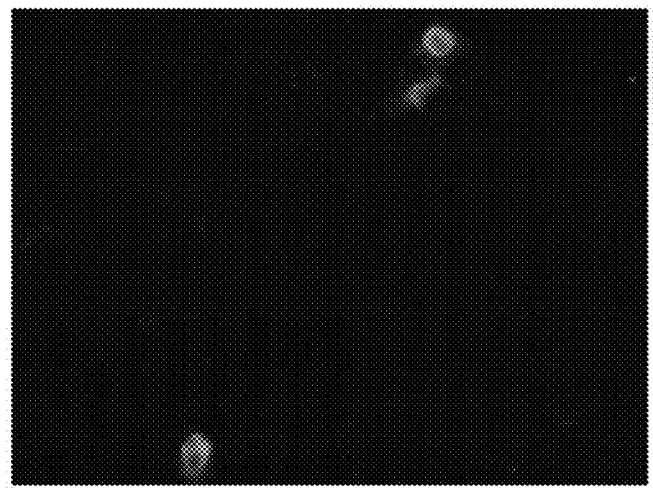
FIG. 14A shows a microscopy image of a BV421-CD14 stain of a prostate cancer cell sample.
Figure 14B:
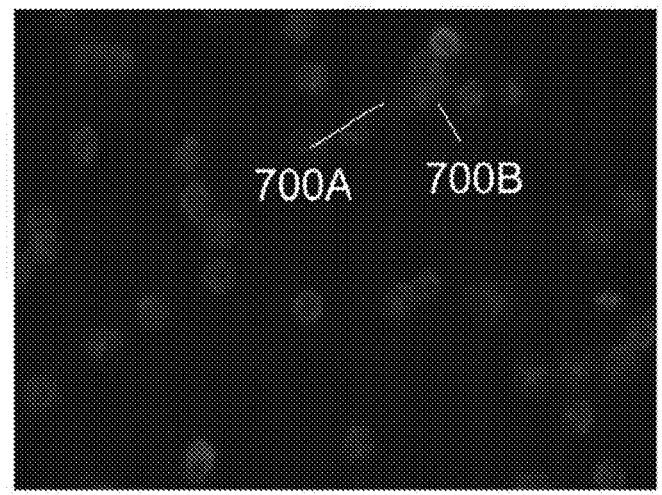
FIG. 14B shows a microscopy image of a Pacific Orange-CD45 stain of a prostate cancer cell sample.
Figure 14C:
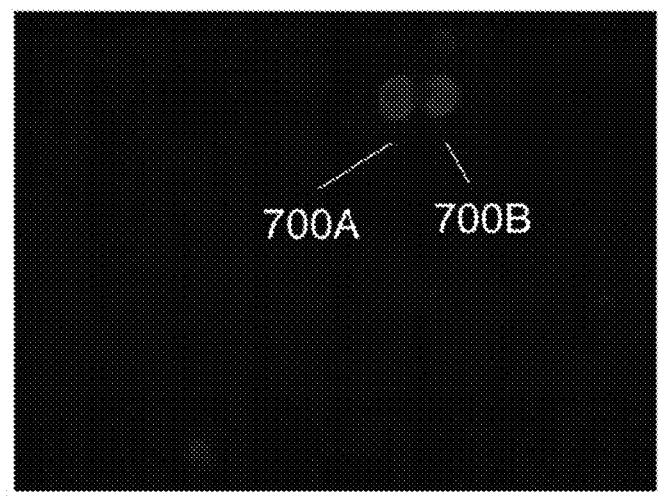
FIG. 14C shows a microscopy image of a AlexaFluor488-Vimentin stain of a prostate cancer cell sample.
Figure 14D:
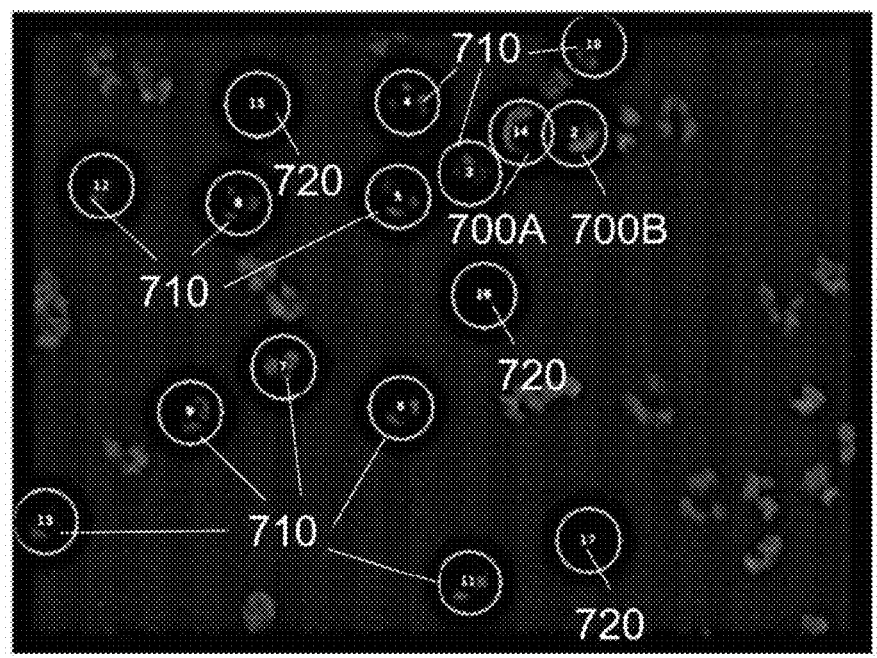
FIG. 14D shows an analysis of a microscopy image including identification of a background area and a nuclear area of cells in a prostate cancer cell sample. The nuclear area is stained with stained with DRAQ5.
Figure 14E:
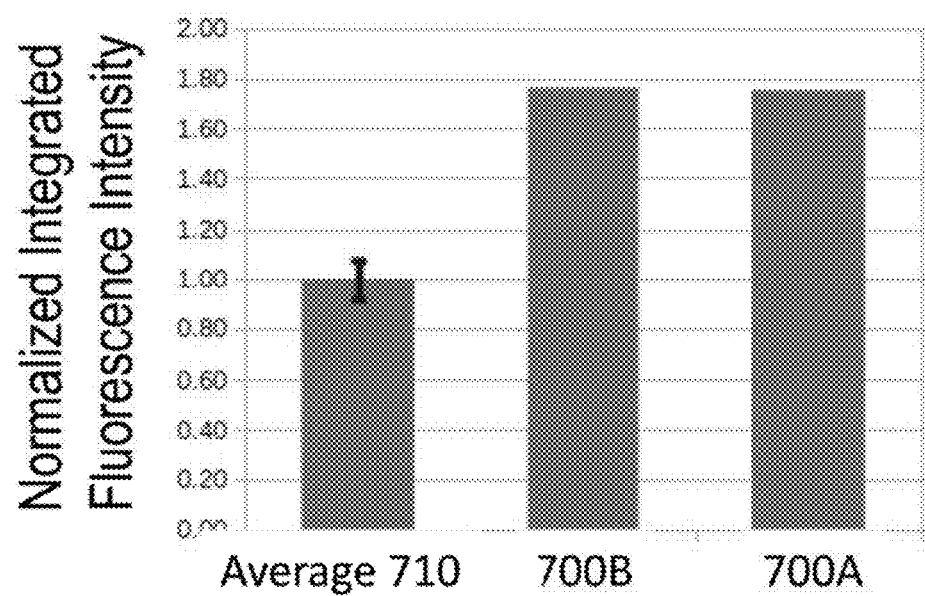
FIG. 14E shows a histogram depicting a ploidy status of a cell of interest.

FIG. 14A shows a microscopy image of a BV421-CD14 stain of a prostate cancer cell sample; FIG. 14B shows a microscopy image of a Pacific Orange-CD45 stain of the same prostate cancer cell sample; and FIG. 14C shows a microscopy image of a AlexaFluor488-Vimentin stain of the same prostate cancer cell sample. In comparing FIGS. 14A-14C, there are two cells of interest 700A, 700B that are staining positive for Vimentin (FIG. 14C) but negative for CD45 (FIG. 14B) and CD14 (FIG. 14A). Nuclear staining of the cells of interest 700A, 700B with DRAQ5 in FIG. 14D reveals that the cells of interest 700A, 700B have an increased DNA content (1.77× and 1.76×, respectively), as shown in the histogram in FIG. 14E, as compared to other cells 710 in the cell sample when the cells of interest 700A, 700B and the other cells 710 are normalized to the background 720, as described in FIGS. 2-3 and elsewhere herein. These data are consistent with the cell of interest either being aneuploidic or a circulating tumor cell. To confirm that the cell is not undergoing healthy mitosis, staining with a proliferation marker or mitosis marker would be required.

Identifying CTC—Example 5

Figure 15A:
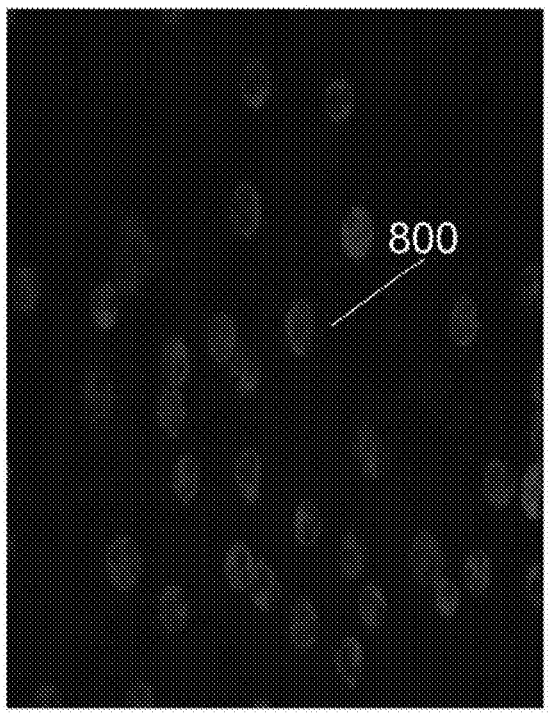
FIG. 15A shows a microscopy image of a AlexaFluor488-CD45 stain of a prostate cancer cell sample.
Figure 15B:
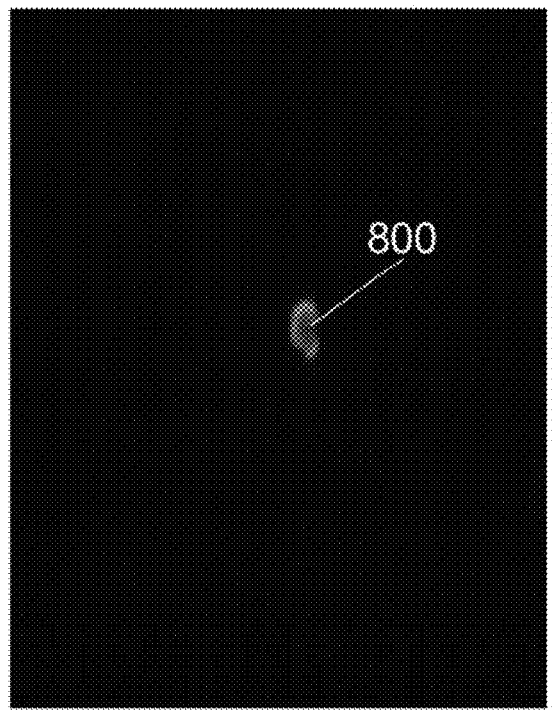
FIG. 15B shows a microscopy image of a PE-phosphorylated serine 10 Histone H3 stain of a prostate cancer cell sample.
Figure 15C:
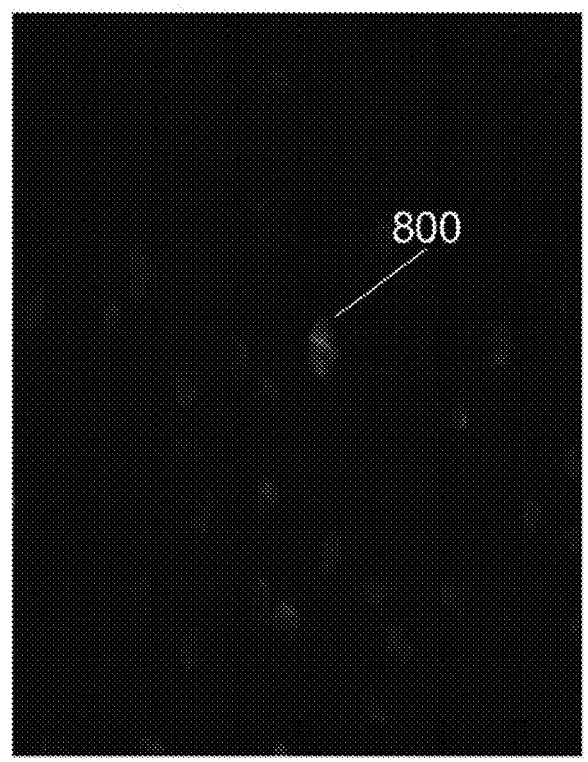
FIG. 15C shows a microscopy image of a AlexaFluor488-Vimentin stain of a prostate cancer cell sample.
Figure 15D:
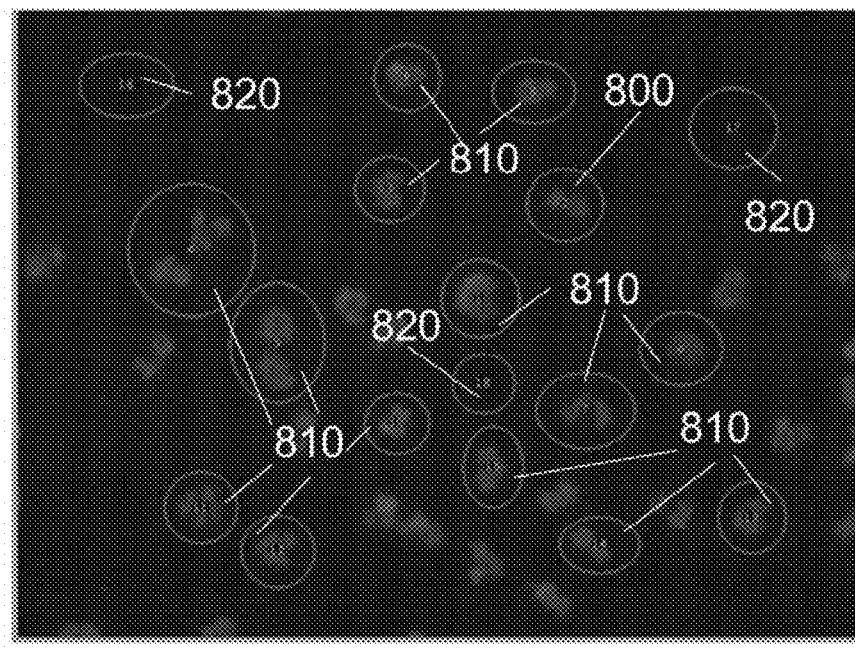
FIG. 15D shows an analysis of a microscopy image including identification of a background area and a nuclear area of cells in a prostate cancer cell sample. The nuclear area is stained with DRAQ5.
Figure 15E:
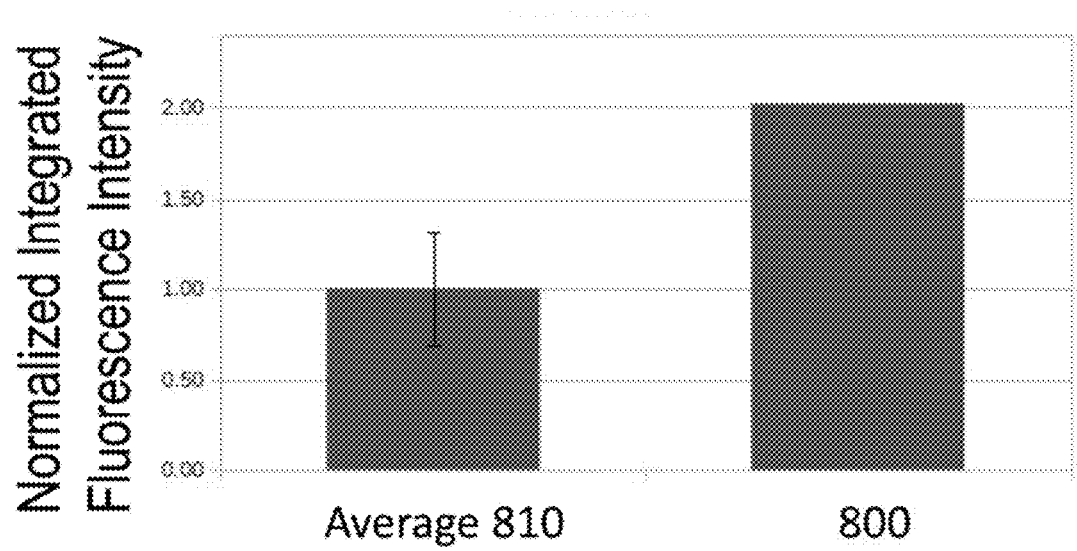
FIG. 15E shows a histogram depicting a ploidy status of a cell of interest.

FIG. 15A shows a microscopy image of a Pacific Orange-CD45 stain of a prostate cancer cell sample; FIG. 15B shows a microscopy image of a PE-phosphorylated serine 10 Histone H3 stain (i.e., a proliferation marker) of the same prostate cancer cell sample; and FIG. 15C shows a microscopy image of a AlexaFluor488-Vimentin stain of the same prostate cancer cell sample. In comparing FIGS. 15A-15C, there is a cell of interest 800 that is staining positive for Vimentin (FIG. 15C), phosphorylated serine 10 Histone H3 (FIG. 15B), and CD45 (FIG. 15A), suggesting that the cell is benign and undergoing mitosis. Nuclear staining of the cell of interest 800 with DRAQ5 as shown in FIG. 15D reveals that the cell of interest 800 has an increased DNA content (2.02×), as shown in the histogram in FIG. 15E, as compared to other cells 810 in the cell sample when the cell of interest 800 and the other cells 810 are normalized to the background 820, as described in FIGS. 2-3 and elsewhere herein. These data are consistent with the cell of interest being benign and in the process of mitosis.

Identifying CTC—Example 6

Figure 16A:
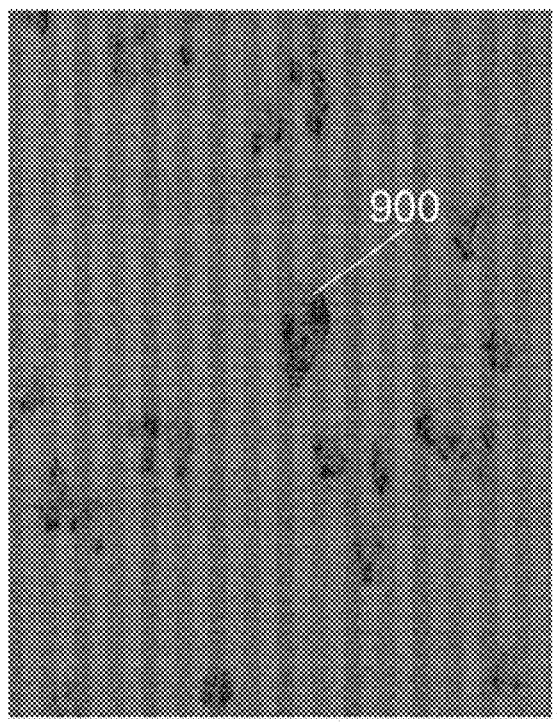
FIG. 16A shows a microscopy image of a BV421-CD34 stain of a prostate cancer cell sample.
Figure 16B:
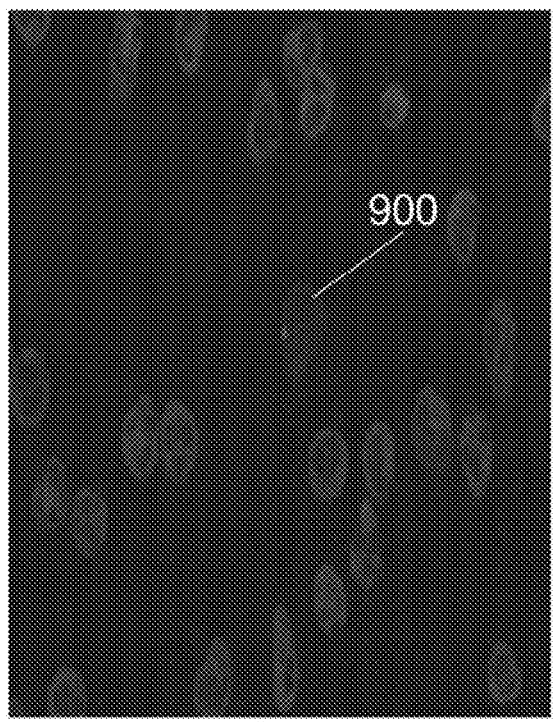
FIG. 16B shows a microscopy image of a Pacific Orange-CD45 stain of a prostate cancer cell sample.
Figure 16C:
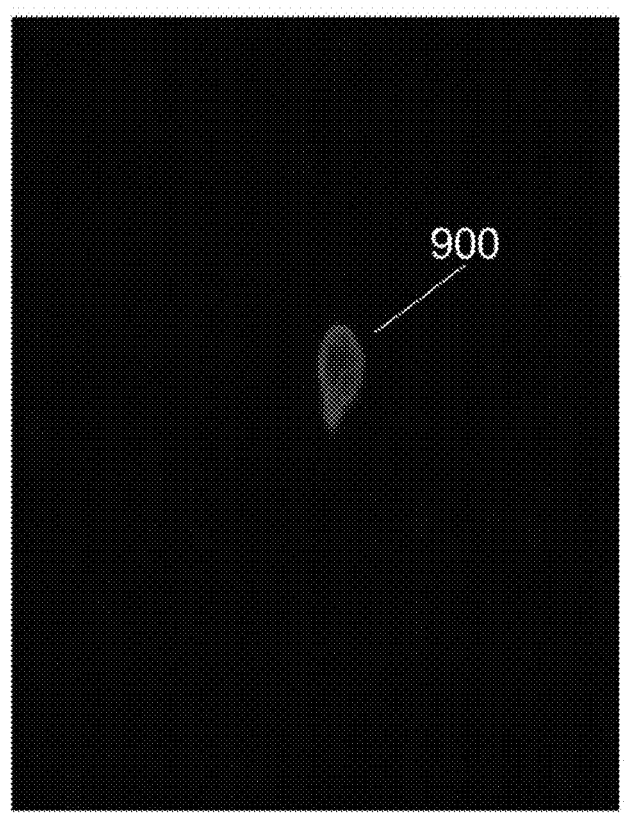
FIG. 16C shows a microscopy image of an AlexaFluor488-Vimentin stain of a prostate cancer cell sample.
Figures 16D, 16E:
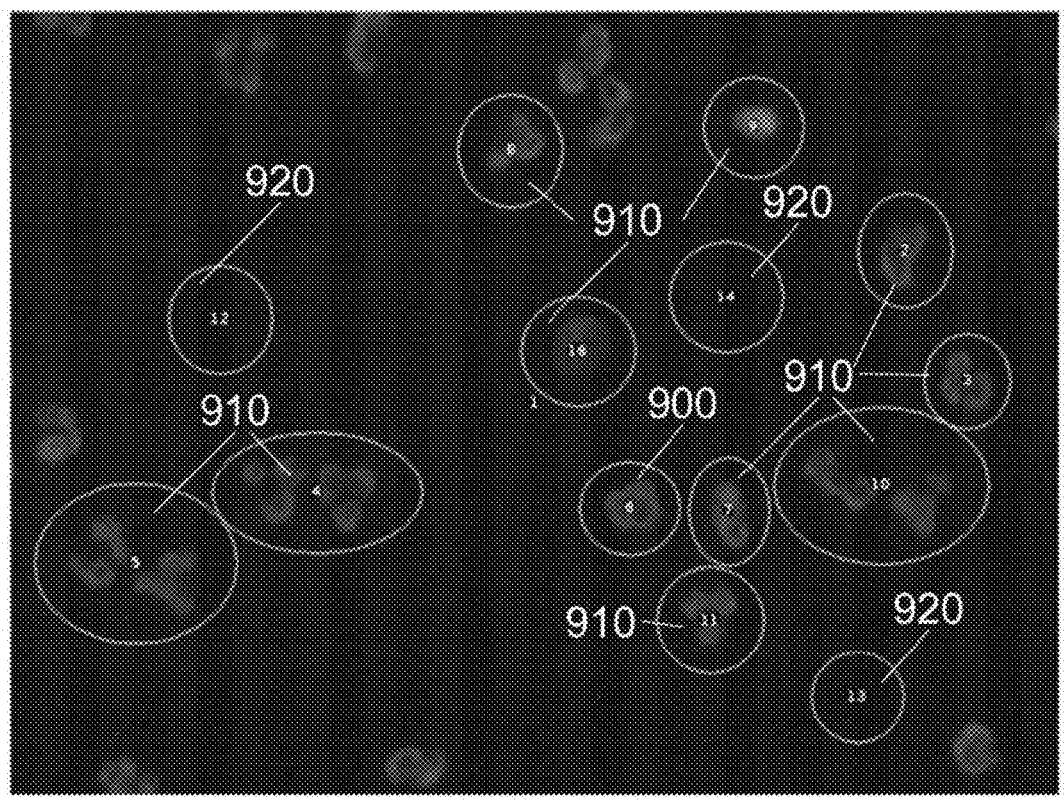
FIG. 16D shows an analysis of a microscopy image including identification of a background area and a nuclear area of cells in a prostate cancer cell sample. The nuclear area is stained with stained with DRAQ5.
FIG. 16E shows a histogram depicting a ploidy status of a cell of interest.

FIG. 16A shows a microscopy image of a BV421-CD34 stain of a prostate cancer cell sample; FIG. 16B shows a microscopy image of a Pacific Orange-CD45 stain of the same prostate cancer cell sample; and FIG. 16C shows a microscopy image of a AlexaFluor488-Vimentin stain of the same prostate cancer cell sample. In comparing FIGS. 16A-16C, there is a cell of interest 900 that is staining positive for Vimentin (FIG. 16C), weakly positive for CD34 (FIG. 16A), but negative for CD45 (FIG. 16B). Nuclear staining of the cell of interest 900 with DRAQ5 as shown in FIG. 16D reveals that the cell of interest 900 has a reduced DNA content (0.83×), as shown in the histogram in FIG. 16E, as compared to other cells 910 in the cell sample when the cell of interest 900 and the other cells 910 are normalized to the background 920, as described in FIGS. 2-3 and elsewhere herein. These data are consistent with the cell of interest being aneuploidic and malignant.

Identifying CTC—Example 7

Figure 17A:
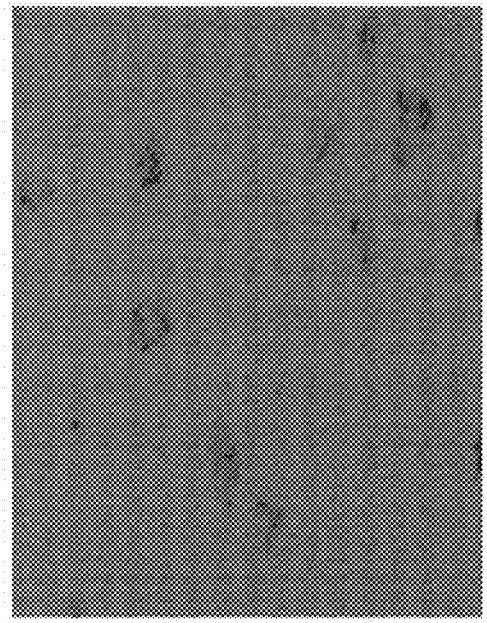
FIG. 17A shows a microscopy image of a BV421-CD14 stain of a prostate cancer cell sample.
Figure 17B:
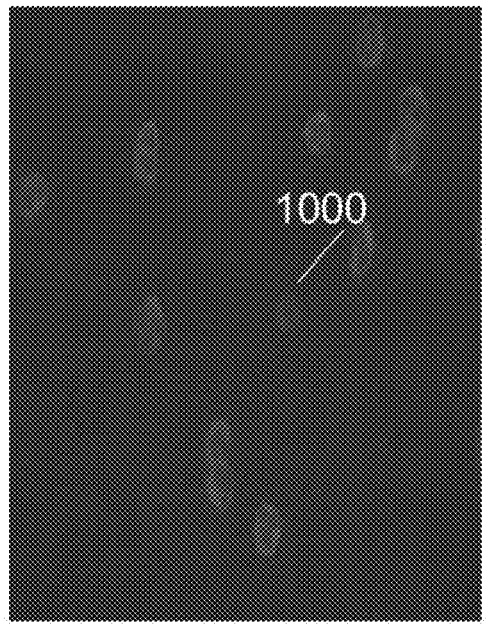
FIG. 17B shows a microscopy image of a Pacific Orange-CD45 stain of a prostate cancer cell sample.
Figure 17C:
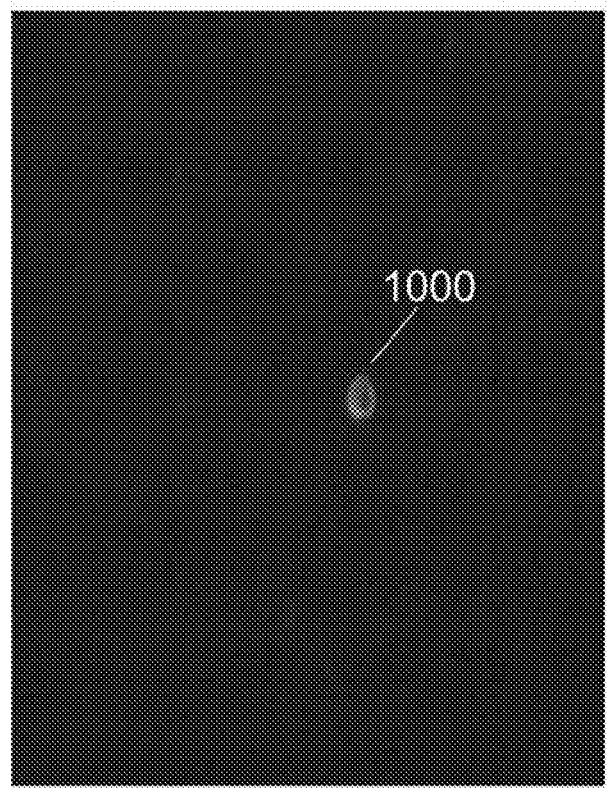
FIG. 17C shows a microscopy image of an AlexaFluor488-Vimentin stain of a prostate cancer cell sample.
Figure 17D:
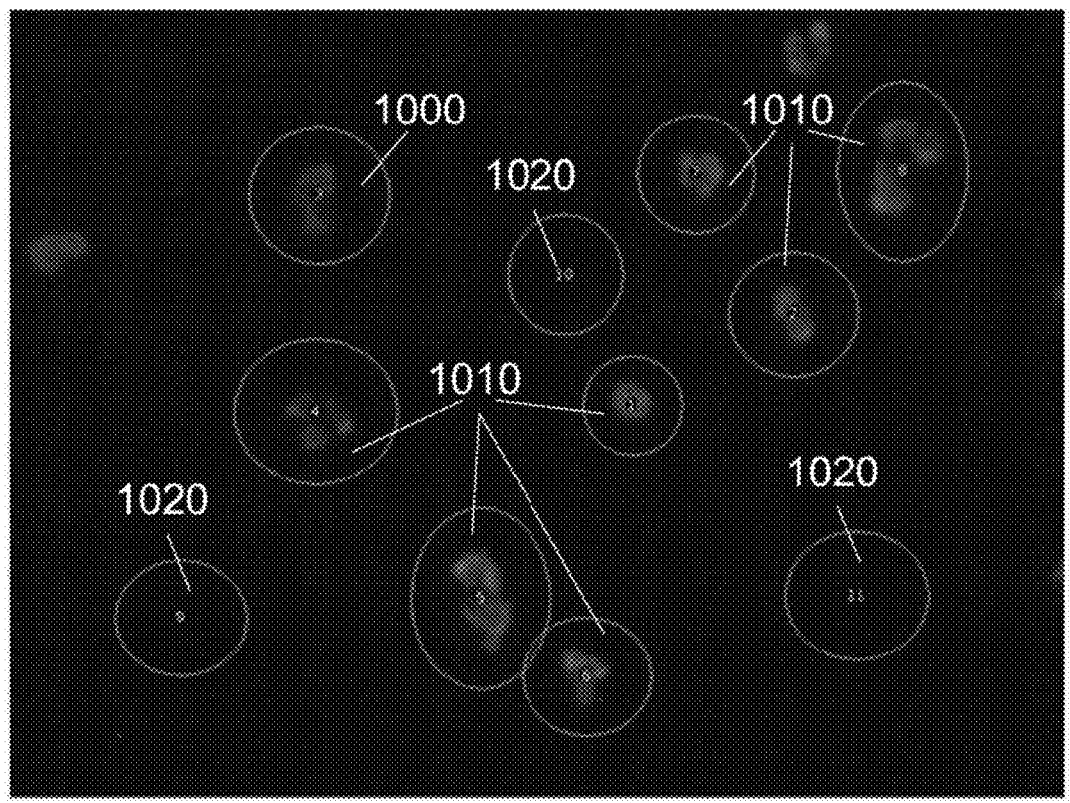
FIG. 17D shows an analysis of a microscopy image including identification of a background area and a nuclear area of cells in a prostate cancer cell sample. The nuclear area is stained with DRAQ5.
Figure 17E:
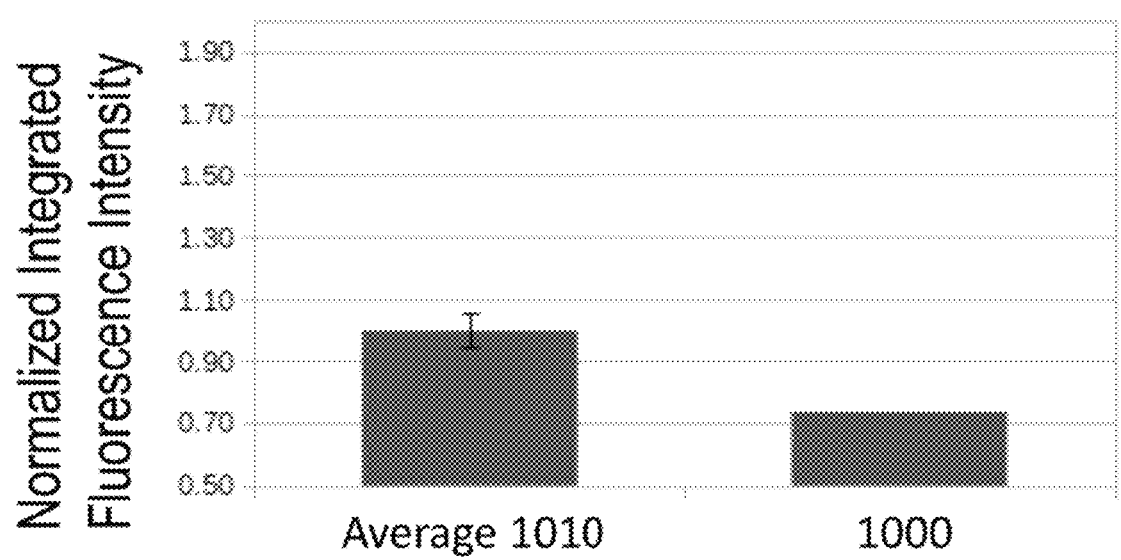
FIG. 17E shows a histogram depicting a ploidy status of a cell of interest.

FIG. 17A shows a microscopy image of a BV421-CD14 stain of a prostate cancer cell sample; FIG. 17B shows a microscopy image of a Pacific Orange-CD45 stain of the same prostate cancer cell sample; and FIG. 17C shows a microscopy image of a AlexaFluor488-Vimentin stain of the same prostate cancer cell sample. In comparing FIGS. 17A-17C, there is a cell of interest 1000 that is staining positive for Vimentin (FIG. 17C), weakly positive for CD45 (FIG. 17B), but negative for CD14 (FIG. 17A). Nuclear staining of the cell of interest 1000 with DRAQ5 as shown in FIG. 17D reveals that the cell of interest 1000 has a reduced DNA content (0.74×), as shown in the histogram in FIG. 17E, as compared to other cells 1010 in the cell sample when the cell of interest 1000 and the other cells 1010 are normalized to the background 1020, as described in FIGS. 2-3 and elsewhere herein. These data are consistent with the cell of interest being aneuploidic and malignant.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer-implemented method of classifying a cell, the computer-implemented method comprising:
acquiring an image of a first cell of interest;
identifying, in the image, a feature associated with the first cell of interest, wherein the feature comprises a first nuclear region;
wherein the identifying comprises:
measuring, in the image, a pixel intensity of a cellular region or marker of the first cell of interest;
determining, in the image, a location of staining of the first cell of interest; and
identifying, in the image, a first nuclear region of the first cell of interest;
processing the feature to extract a parameter of interest, wherein the parameter of interest comprises a first fluorescence intensity, or a first pixel intensity, of the first nuclear region; wherein processing the feature further comprises:
subtracting a background fluorescence intensity or a background pixel intensity from the first fluorescence intensity, or the first pixel intensity, of the first nuclear region, and
normalizing staining intensity across cells in the image by comparing the first fluorescence intensity, or the first pixel intensity, of the first nuclear region in the first cell of interest to a second fluorescence intensity, or a second pixel intensity, of a second nuclear region of a second cell of interest in the image;
analyzing the parameter of interest, the analyzing comprising:
determining whether the parameter of interest is less than one or greater than two indicative of abnormally low or abnormally high DNA content, or
determining whether the parameter of interest is between one to two, indicative of a normal DNA content level, and the first cell of interest is negative for a proliferation marker; and
classifying, based on the analyzing, the first cell of interest as a circulating tumor cell or as a healthy cell.

2. The computer-implemented method of claim 1, further comprising identifying whether the first cell of interest expresses one or both of: vimentin and CD45.

3. The computer-implemented method of claim 1, wherein the first cell of interest is CD45 negative and vimentin positive.

4. The computer-implemented method of claim 1, further comprising:
identifying the first cell of interest as an apoptotic cell as being Caspase 3 positive; and
excluding the apoptotic cell.

5. The computer-implemented method of claim 1, further comprising:
identifying the first cell of interest as a mitotic cell as having phosphorylated H3 or Ki-67; and
excluding the mitotic cell.

6. The computer-implemented method of claim 1, further comprising calculating a confidence score for the classification of the first cell of interest.

7. The computer-implemented method of claim 1, wherein:
the first cell of interest is classified as a circulating tumor cell in response to determining that the parameter of interest is less than one or greater than two, indicative of abnormally low or abnormally high DNA content, or
the first cell of interest is classified as a circulating tumor in response to determining that the parameter of interest is within one to two, indicative of a normal DNA content level, and the first cell of interest is negative for a proliferation marker; and otherwise the first cell of interest is classified as a healthy cell.

8. A computer-implemented method of classifying a cell, the method comprising:
acquiring an image of a first cell of interest;
identifying a feature associated with the first cell of interest, wherein the feature comprises a first nuclear region,
wherein the identifying comprises:
measuring, in the image, a pixel intensity of a cellular region or marker of the first cell of interest;
determining, in the image, a location of staining of the first cell of interest; and
identifying, in the image, a first nuclear region of the first cell of interest;
processing the feature to extract a parameter of interest, wherein the parameter of interest comprises a first fluorescence intensity, or a first pixel intensity, of the first nuclear region;
wherein processing the feature further comprises:
subtracting a background fluorescence intensity or a background pixel intensity from the first fluorescence intensity, or the first pixel intensity, of the first nuclear region, and
normalizing staining intensity across cells in the image by comparing the first fluorescence intensity, or the first pixel intensity, of the first nuclear region in the first cell of interest to a second fluorescence intensity, or a second pixel intensity, of a second nuclear region of a second cell of interest in the image;

analyzing the parameter of interest with at least one machine learning technique, the analyzing comprising:
determining whether the parameter of interest is less than one or greater than two indicative of abnormally low or abnormally high DNA content, or
determining whether the parameter of interest is between one to two, indicative of a normal DNA content level, and the first cell of interest is negative for a proliferation marker; and
classifying, based on the analyzing, the first cell of interest as a circulating tumor cell or as a healthy cell.

9. The computer-implemented method of claim 8, wherein the at least one machine learning technique comprises: Classification Trees, Discriminant Analysis, k-Nearest Neighbors, Naive Bayes, Support Vector Machines, deep learning, or convolutional neural network.

10. The computer-implemented method of claim 8, further comprising calculating a confidence score for the classification of the first cell of interest.

11. The computer-implemented method of claim 8, wherein:
the first cell of interest is classified as a circulating tumor cell in response to determining that the parameter of interest is less than one or greater than two, indicative of abnormally low or abnormally high DNA content, or
the first cell of interest is classified as a circulating tumor in response to determining that the parameter of interest is within one to two, indicative of a normal DNA content level, and the first cell of interest is negative for a proliferation marker; and
otherwise the first cell of interest is classified as a healthy cell.

* * * * *